United States Patent
Smith et al.

(10) Patent No.: US 9,701,932 B2
(45) Date of Patent: *Jul. 11, 2017

(54) AUTOMATED TISSUE ENGINEERING SYSTEM

(71) Applicant: Octane Biotech Inc., Kingston (CA)

(72) Inventors: Timothy J. N. Smith, Kingston (CA); Sydney M. Pugh, Glenburnie (CA); Martin R. Pecaric, Kingston (CA); Rupert Hagg, Winterthur (CH); Roberto Tommasini, Uster (CH); Yves Larcher, Schileren (CH); Lowell D. Misener, Kingston (CA)

(73) Assignee: Octane Biotech Inc., Kingston (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/906,698

(22) Filed: May 31, 2013

(65) Prior Publication Data

US 2014/0193895 A1  Jul. 10, 2014

Related U.S. Application Data

(62) Division of application No. 10/510,777, filed as application No. PCT/CA03/00519 on Apr. 8, 2003, now Pat. No. 8,492,140.

(60) Provisional application No. 60/370,209, filed on Apr. 8, 2002.

(51) Int. Cl.
| | |
|---|---|
| *C12M 3/00* | (2006.01) |
| *C12M 1/12* | (2006.01) |
| *C12M 1/36* | (2006.01) |
| *C12M 1/00* | (2006.01) |

(52) U.S. Cl.
CPC .......... *C12M 21/08* (2013.01); *C12M 23/42* (2013.01); *C12M 23/52* (2013.01); *C12M 25/14* (2013.01); *C12M 41/48* (2013.01)

(58) Field of Classification Search
None
See application file for complete search history.

(56) References Cited

U.S. PATENT DOCUMENTS

| | | | |
|---|---|---|---|
| 5,041,138 A | 8/1991 | Vacanti et al. | |
| 5,081,036 A | 1/1992 | Familletti | |
| 5,688,687 A | 11/1997 | Palsson et al. | |
| 5,728,581 A | 3/1998 | Schwartz et al. | |
| 5,792,603 A | 8/1998 | Dunkelman et al. | |
| 5,827,729 A | 10/1998 | Naughton et al. | |
| 5,842,477 A | 12/1998 | Naughton et al. | |
| 5,846,828 A | 12/1998 | Peterson et al. | |
| 5,882,929 A | 3/1999 | Fofonoff et al. | |
| 5,891,455 A | 4/1999 | Sittinger et al. | |
| 5,902,741 A | 5/1999 | Purchio et al. | |
| 5,989,913 A | 11/1999 | Anderson et al. | |
| 5,994,129 A | 11/1999 | Armstrong et al. | |
| 6,048,721 A | 4/2000 | Armstrong et al. | |
| 6,048,722 A | 4/2000 | Farb et al. | |
| 6,060,306 A | 5/2000 | Flatt et al. | |
| 6,121,042 A | 9/2000 | Peterson et al. | |
| 6,228,635 B1 | 5/2001 | Armstrong et al. | |
| 6,323,146 B1 | 11/2001 | Pugh et al. | |
| 2001/0043918 A1 | 11/2001 | Masini et al. | |
| 2002/0009797 A1 | 1/2002 | Wolf et al. | |
| 2002/0025547 A1 | 2/2002 | Rao | |
| 2005/0058632 A1* | 3/2005 | Hedrick et al. | 424/93.7 |

FOREIGN PATENT DOCUMENTS

| | | |
|---|---|---|
| AU | 2002/324169 | 3/2003 |
| DE | 4021123 | 4/1991 |
| EP | 0248675 | 5/1995 |
| GB | 1356794 | 6/1974 |
| WO | 97/12960 | 5/1997 |
| WO | 99/47922 | 9/1999 |
| WO | 00/46349 | 6/2000 |
| WO | 01/00783 | 1/2001 |
| WO | 02/28996 | 4/2002 |
| WO | 03/085101 | 10/2003 |

* cited by examiner

*Primary Examiner* — Thane Underdahl
(74) *Attorney, Agent, or Firm* — Shumaker, Loop & Kendrick, LLP

(57) ABSTRACT

The invention provides systems, modules, bioreactor and methods for the automated culture, proliferation, differentiation, production and maintenance of tissue engineered products. In one aspect is an automated tissue engineering system comprising a housing, at least one bioreactor supported by the housing, the bioreactor facilitating physiological cellular functions and/or the generation of one or more tissue constructs from cell and/or tissue sources. A fluid containment system is supported by the housing and is in fluid communication with the bioreactor. One or more sensors are associated with one or more of the housing, bioreactor or fluid containment system for monitoring parameters related to the physiological cellular functions and/or generation of tissue constructs; and a microprocessor linked to one or more of the sensors. The systems, methods and products of the invention find use in various clinical and laboratory settings.

22 Claims, 23 Drawing Sheets

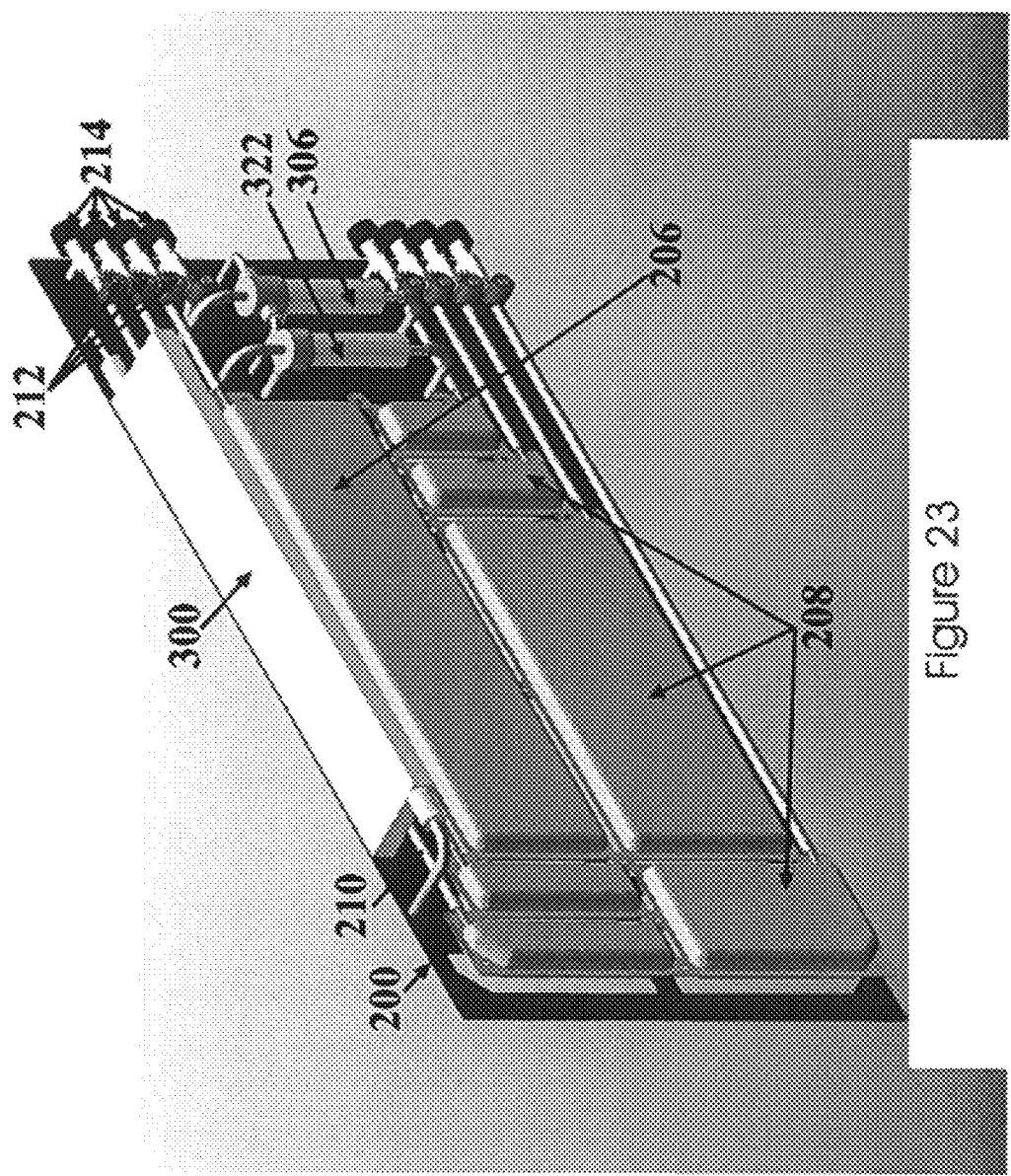

AUTOMATED TISSUE ENGINEERING SYSTEM

CROSS-REFERENCE TO RELATED APPLICATIONS

This application is a divisional of U.S. patent application Ser. No. 10/510,777 (incorporated herein by reference in its entirety) filed on Sep. 29, 2005, which is a national phase entry of International Application No. PCT/CA03/00519 (incorporated herein by reference in its entirety) filed on Apr. 8, 2003 that claims priority to U.S. Provisional Application Ser. No. 60/370,209 (incorporated herein by reference in its entirety) filed on Apr. 8, 2002. Throughout this application various publications are referenced. The disclosures of these publications in their entireties are hereby incorporated by reference into this application in order to describe more fully the state of the art to which the invention pertains.

This invention relates to devices, methods and systems for the automated culture, proliferation, differentiation, production and maintenance of tissue engineered products. Such systems, methods and products find use in various clinical and laboratory settings.

BACKGROUND OF THE INVENTION

Throughout this application, various references are cited in parentheses to describe more fully the state of the art to which this invention pertains. The disclosures of these references are hereby incorporated by reference into the present disclosure.

During the past several years, researchers have developed and used different cell culture and tissue engineering techniques for the culture and production of various types of cellular implants. Such systems are described for example in U.S. Pat. Nos. 5,041,138, 5,842,477, 5,882,929, 5,891,455, 5,902,741, 5,994,129, 6,048,721 and 6,228,635. Bioreactor systems have also been developed for the culture of cells and cellular implants and are described for example in U.S. Pat. Nos. 5,688,687, 5,728,581, 5,827,729 and 6,121,042.

The aforementioned methods and systems generally employ conventional laboratory culturing techniques using standard culture equipment for cell seeding of selected cell populations onto scaffolds. As such, the generated implants simply comprise proliferated cell populations grown on a type of biopolymer support where any manipulation of the cellular environment is limited to endogenous cell production of cytokines present in any standard cell culture, and application of shear and/or physical stresses due to circulation of cell culture media and physical manipulation of the support onto which the cells are seeded. The systems do not address nor are they capable of generating a tissue implant that comprises proliferated and differentiated cells representative of developing tissues in vivo and further integrated within a selected scaffold that can be successfully integrated in viva. Moreover, known methods and systems are not capable of multi-functionally carrying out all of the steps of biopsy tissue digestion to yield disassociated cells, subsequent cell seeding on a proliferation substrate, cell number expansion, controlled differentiation, tissue formation and production of a tissue implant within a single automated tissue engineering system. This is primarily because known culture systems are not sophisticated in that they are not capable of automatically evaluating and manipulating the changing environment surrounding the developing implant such that cells progressively proliferate and differentiate into a desired implant.

Furthermore, conventional culture methods and systems are labor Intensive and suffer from the drawbacks of contamination and varying degrees of culturing success due to human error and lack of continual performance evaluation. Conventional culture systems require that most of the initial steps in the preparation of cells for seeding (i.e. tissue digestion, cell selection) is performed manually which is time consuming, unreliable in terms of the quality of the tissue produced, and prone to culture contamination problems. The systems are incapable of supporting the automated preparation of tissue engineered implants from primary or precursor cells due to inherent design limitations that restrict the cell and tissue culture process, the inability to adequately monitor and modify the environment to support tissue development, and the absence of techniques to enable the implementation of effective quality control measures.

Thus, there remains a real and unmet need for an improved system for in vitro and ex vivo tissue engineering that can consistently meet the operational requirements associated with the different steps in the development and production of tissue engineered implants. Of particular importance is the ability to create functional tissue constructs where the cells present are active, differentiated and already expressing extracellular matrix. This involves more than, and is strikingly different to, the simple simulation of the mature in vivo environment present at the host site. This is because the preparation of functional de novo tissue fundamentally requires that the cells progress through a series of developmental stages as part of an ex vivo sequence.

In order to address both clinical and research requirements, new devices, methods and systems have been developed that obviate several of the disadvantages and limitations of conventional ex viva culturing techniques and systems.

SUMMARY OF THE INVENTION

The present invention is directed to a user-friendly automated system for cell culture and tissue engineering that can be used in a variety of clinical and research settings for both human and veterinary applications.

As used herein, "tissue engineering" may be defined as "the application of principles and methods of engineering and life sciences toward fundamental understanding and development of biological substitutes to restore, maintain and improve tissue functions". This definition is intended to include procedures where the biological substitutes are cells or combinations of different cells that may be implanted on a substrate or scaffold formed of biocompatible materials to form a tissue, in particular an implantable tissue construct. Furthermore, it is noted that the cells involved in the tissue engineering processes may be autologous, allogenic or xenogenic.

The tissue engineering system of the present invention is designed to perform all activities under sterile operating conditions. The system is fully automated, portable, multi-functional in operation and performs/provides one or more of the following:
  sterile reception/storage of tissue biopsy;
  automated monitoring of digestion process
  digestion of biopsy tissue to yield disassociated cells;
  cell sorting and selection, including safe waste collection;
  cell seeding on or within a proliferation substrate or scaffold
  proliferation of cells to expand cell populations;
  cell washing and cell collection;

cell seeding on or within a tissue engineering scaffold or matrix;

cell differentiation to allow specialization of cellular activity;

tissue formation;

mechanical and/or biochemical stimulation to promote tissue maturity;

harvesting the tissue engineered constructs/implants for reconstructive surgery; and storage and transportation of implantable tissue.

The tissue engineering system of the present invention may be pre-programmed to perform each of the above noted steps, individually, sequentially or in certain predetermined partial sequences as desired and required. Furthermore, each of these steps, or any combination thereof, are accomplished within one or more bioreactors on a tissue engineering module. In operation, the tissue engineering system is pre-programmed and automatically controlled thus requiring minimal user intervention and, as a result, enhances the efficiency and reproducibility of the cell culture and/or tissue engineering process while minimizing the risks of contamination. The tissue engineering system of the invention and components thereof are operable under conditions of microgravity and/or zero gravity where such system and components are used for space research.

The system of the present invention is designed such that primary or precursor cells can be isolated from a donor tissue for further propagation, differentiation and production of a tissue implant. Alternatively, cell lines may also be used either alone or in combination with other cell sources.

In accordance with the invention, is an automated tissue engineering system, the system comprising a housing that supports at least one bioreactor that facilitates physiological cellular functions and the generation of tissue constructs from cell and tissue sources. The housing also supports a fluid containment system that is in fluid communication with the bioreactor. Associated with the housing and/or the bioreactor are sensors that monitor physiological parameters of fluid provided in the fluid containment system. A microprocessor disposed within the housing is linked to the bioreactor and the fluid containment system and functions to control their functioning. The microprocessor may also independently control environmental conditions within the system.

In accordance with another aspect of the invention there is provided a system for cell and tissue engineering comprising portable, sterile tissue engineering modules having one or more bioreactors which provide the basis for tissue digestion, cell seeding on a proliferation substrate, cell proliferation, cell seeding on a differentiation scaffold, cell differentiation, and tissue formation with subsequent maturation into functional tissue for implantation. The bioreactor is operatively connected with a media flow and reservoir system for the delivery of reagents and the collection of waste fluids in a non-reflux manner. The bioreactor and/or the media flow system optionally include gas exchange components that utilize semi-permeable membranes to allow the transfer of gaseous products thereby controlling levels of dissolved gases in the media. The tissue engineering module operatively interacts with a central microprocessor controlled base unit that automatically monitors the progression of the cell culture or tissue engineering process and adjusts the environmental conditions to meet the requirements of the different stages of cell culture and tissue development within the bioreactor. Deviations from ideal conditions are sensed by a variety of sensors present within the bioreactor and the signals generated are monitored by the central microprocessor. As such, changes in environmental conditions such as but not limited to pH, temperature and dissolved gases can be automatically monitored and altered as required. In addition, the status of cell proliferation is indirectly assessed by detection of metabolic turnover as a function of time (e.g. pH, $O_2$, $CO_2$, lactic acid and glucose consumption). Further to the control of processing conditions by the central microprocessor, the tissue engineering module itself may optionally include a secondary onboard microprocessor that operates in unison with the central microprocessor. The tissue engineering module microprocessor expands the data processing capabilities of the tissue engineering system by performing specific functions directly onboard the tissue engineering module, thereby minimizing the demands on the central microprocessor.

Various growth factors, cytokines, experimental agents, pharmaceuticals, chemicals, culture fluids and any combinations thereof may be loaded and stored within any of the reservoirs located on the tissue engineering module and automatically transferred to the one or more bioreactors according to a pre-programmed sequence or as required by the developing tissue implant. The individual tissue engineering modules are removable from the system for transport without compromising the sterility of the tissue engineered constructs present within the bioreactor. Such removal does not affect the processing of any other modules present within the tissue engineering system. Furthermore, the tissue engineering module may be considered to be disposable following the completion of a tissue engineering sequence, as this practice prevents contamination arising from prior use.

In various embodiments of the invention, the device and system can be used to digest tissues obtained by surgical biopsy. In another embodiment, cells can be filtered and a particular population selected and isolated. In another embodiment, digested cells can be proliferated to expand the population of the cells. In still a further embodiment, cells can be seeded and cultivated on a desired scaffold or substrate (also referred to as a matrix). In yet a further embodiment, cells can be differentiated on and/or throughout a desired scaffold or substrate until suitable tissue formation is obtained. In yet a further embodiment, the tissue may be stimulated to promote tissue maturity. In yet another embodiment, a tissue implant is produced that is suitable for reconstructive surgery. In still a further embodiment, cell sampling can be done at each stage of cellular proliferation and developmental progression in a sterile manner without adverse effects on the culture itself. Each of the aforementioned embodiments can be done alone or sequentially as desired. Tracking of such processing events can be performed by the central microprocessor and/or the module-based microprocessor for incorporation into quality control records.

In one aspect, the tissue engineering system optionally uses a synthetic biomaterial compound, Skelite™, described in Applicant's U.S. Pat. No. 6,323,146 (the contents of which are herein incorporated by reference) to enhance biological performance. Briefly, Skelite™ is an isolated bioresorbable biomaterial compound comprising calcium, oxygen and phosphorous, wherein a portion of at least one of said elements is substituted with an element having an ionic radius of approximately 0.1 to 0.6 Angstroms. In one embodiment, Skelite™ may be used to enhance cell proliferation through its use as a coating on the walls of the bioreactor, as a thin film on the proliferation substrate, or as a three-dimensional and thereby high surface area proliferation scaffold The use of Skelite™ in the proliferation stage may be demonstrated to:

increase the rate of proliferation;

increase the cell yield following the proliferation step;

reduce the surface area required for a target cell yield;

reduce the problematic tendency of cell phenotype dedifferentiation during proliferation; and enhance the binding of growth factors to the proliferation substrate.

In a further embodiment, Skelite™ may be used as a resorbable scaffold to enhance the differentiation of cells and the subsequent formation of tissue constructs. The use of Skelite™ in the differentiation stage may be demonstrated to:

increase productivity by improving the reliability of the differentiation stage;

increase the integrity and hence biological viability of the tissue construct;

allow flexibility in construct configuration based on various scaffold formats;

allow the stages of proliferation, differentiation and tissue formation to occur on a common substrate;

enhance the binding of growth factors to the differentiation scaffold; and

Improve tissue construct handling properties during surgical implantation.

In another aspect, the present invention provides a method and system for the preparation of tissue constructs through the automated steps of digestion, proliferation, seeding and differentiation of primary or precursor cells that originate from a patient thus eliminating immunological and disease transmission issues. An implant may be formed from the controlled cultivation of various cell types, including but not limited to chondrocytes, stromal cells, osteoblasts, nerve cells, epithelial cells stem cells and mixtures thereof.

The system of the invention in an embodiment, incorporates one or more detachable, portable, and independently operable tissue engineering modules that support one or more bioreactors, media reservoirs and fluid/media flow system. Each module, and hence the bioreactor(s), is under the automated control of a central microprocessor. The module and associated bioreactor(s) may be configured for various specialized applications such as, but not limited to:

sterile reception/storage of tissue biopsy;

automated mixing and delivery of digestion reagents;

automated monitoring of digestion process;

digestion of biopsy tissue to yield disassociated cells;

cell sorting and selection, including safe waste collection;

cell washing and cell collection;

cell seeding on or within a proliferation substrate or scaffold;

automated mixing and delivery of proliferation reagents;

proliferation of cells to expand cell populations;

automated monitoring of cell conditions, including detection of confluence;

controlled cell release from the proliferation substrate or scaffold;

repeated proliferation steps on selected surface area sizes to increase cell numbers;

channeling of cell population toward one or more tissue engineering scaffolds or matrices;

cell seeding on or within the tissue engineering scaffold or matrix;

automated mixing and delivery of differentiation reagents;

automatic monitoring of cell/tissue culture conditions;

cell differentiation to allow specialization of cellular activity;

tissue formation;

mechanical and/or biochemical stimulation to promote tissue maturity;

harvesting the tissue engineered constructs/implants for reconstructive surgery; and storage and transportation of cells and/or implantable tissue.

When two or more bioreactors are provided within the system either supported directly within the housing of the system or supported on a tissue engineering module insertable into the housing, the bioreactors may be provided connected in series and individually operable and controlled by the microprocessor or alternatively, may be operated and controlled independently depending on the user's programming of the microprocessor and the desired result to be achieved. Furthermore, when two or more bioreactors are provided within the system, the bioreactors and internal chambers may be connected such that there is an exchange of cells and/or tissues from bioreactor to bioreactor.

The bioreactor can be manufactured in various sizes and configurations as required to support varying numbers and sizes of proliferation and differentiation scaffolds or substrates. The bioreactor may be incorporated as part of the structural components of the tissue engineering module. Alternately, the bioreactor may be detachable as a separate component to the remaining components of tissue engineering module. If present as a discrete component, the bioreactor may be packaged separately in a sterile package and joined to the tissue engineering module using sterile access techniques at the time of use. Furthermore, the sterile access techniques enable the bioreactor to be detached from the module, upon completion of the tissue engineering process, for easy transport to the operating room in preparation for the retrieval of a newly formed implantable tissue construct.

The bioreactor and/or the tissue engineering module may be rotated or agitated within the overall tissue engineering system via control actuators. Rotation may enable the beneficial use of gravity to effect specific bioprocessing sequences such as sedimentation-based cell seeding and fluid exchange within the bioreactor.

The tissue engineering module may be bar coded or provided with a memory chip for rapid and accurate tracking both within the tissue engineering system and externally as part of the clinical or experimental environment. Such tracking technology as incorporated within the tissue engineering device also enables electronic tracking via clinic-based information systems for patient records. This ensures that the tissue engineering module and hence the associated cells or tissue implants are properly coded to ensure administration to the correct patient and that the process is recorded for hospital billing purposes. The module and/or bioreactor may also utilize a bar code and/or memory chip in a similar manner for rapid and accurate patient and sample tracking.

According to an aspect of the present invention is an automated tissue engineering system comprising;

a housing;

at least one bioreactor supported by said housing, said bioreactor facilitating physiological cellular functions and/or the generation of one or more tissue constructs from cell and/or tissue sources;

a fluid containment system supported by said housing and in fluid communication with said bioreactor, one or more sensors associated with one or more of said housing, bioreactor or fluid containment system for monitoring parameters related to said physiological cellular functions and/or generation of tissue constructs; and a microprocessor linked to one or more of said sensors.

According to another aspect of the present invention is an automated tissue engineering system comprising;

a housing;

at least one tissue engineering module removably accommodated within said housing, said tissue engineering module comprising a support structure that holds at least one bioreactor, said bioreactor facilitating physiological cellular functions and/or the generation of one or more tissue constructs from cell and/or tissue sources, a fluid containment system in fluid communication with said bioreactor, and one or more sensors for monitoring parameters related to said cell culture and/or tissue engineering functions; and a microprocessor disposed in said housing and linked to said tissue engineering module, said microprocessor controlling the operation of said tissue engineering module.

According to a further aspect of the invention is portable and sterilizable tissue engineering module, the module comprising;

a structural support holding at least one bioreactor, said bioreactor facilitating cell culture and tissue engineering functions;

a fluid containment system in fluid communication with said bioreactor; and one or more sensors for monitoring parameters related to said cell culture and tissue engineering functions.

In aspects of this embodiment, the bioreactor comprises a bioreactor housing having one or more inlet ports and one or more outlet ports for media flow and at least one chamber defined within said bioreactor housing for receiving cells and/or tissues and facilitating said cell culture and tissue engineering functions. The chamber may be selected from the group consisting of a cell culture/proliferation chamber, cell differentiation/tissue formation chamber, tissue digestion chamber and combinations thereof. Furthermore, the chamber houses one or more substrates and/or scaffolds. In embodiments of the invention, two or more chambers may be provided operably connected within the bioreactor and be operably connected. Alternatively, the two or more bioreactors may be independently operable or co-operatively operable. In still further aspects, the chambers and/or bioreactors are operably connected to provide for the exchange of fluids, cells and/or tissues between the chambers and/or bioreactors. The scaffold for use in the present invention is selected from the group consisting of a porous scaffold, a porous scaffold with gradient porosity, a porous reticulate scaffold, a fibrous scaffold, a membrane encircled scaffold and combinations thereof. Chambers may also be further subdivided into zones. For example, a differentiation/tissue formation chamber may be provided with a plurality of zones to contain several scaffolds. Funnels or similar passageways may be provided between chambers within a bioreactor. Furthermore, one or more filters may be provided at any location within a bioreactor.

According to still another aspect of the present invention is a bioreactor that provides an environment for cell culture and/or tissue engineering functions selected from the group consisting of storage of tissue biopsy, digestion of tissue biopsy, cell sorting, cell washing, cell concentrating, cell seeding, cell proliferation, cell differentiation, cell storage, cell transport, tissue formation, implant formation, storage of implantable tissue, transport of implantable tissue and combinations thereof.

According to still another aspect of the present invention is a bioreactor for facilitating and supporting cellular functions and generation of implantable tissue constructs, said bioreactor comprising;

a bioreactor housing;

one or more inlet ports and one or more outlet ports for media flow;

at least one chamber defined within said bioreactor housing for facilitating and supporting cellular functions and/or the generation of one or more tissue constructs from cell and/or tissue sources; and one or more sensors for monitoring parameters related to said cellular functions and/or generation of tissue constructs within said at least one chamber.

In embodiments of the invention, the bioreactor housing comprises a lid, where the lid may be a detachable lid or integral with the bioreactor housing.

Cells and tissues may be selected from bone, cartilage, related bone and cartilage precursor cells and combinations thereof. More specifically, cells suitable for use in the bioreactor, module and system of the invention are selected from but not limited to the group consisting of embryonic stem cells, adult stem cells, osteoblastic cells, pre-osteoblastic cells, chondrocytes, nucleus pulposus cells, pre-chondrocytes, skeletal progenitor cells derived from bone, bone marrow or blood, including stem cells, and combinations thereof. The cells or tissues may be of an autologous, allogenic, or xenogenic origin relative to the recipient of an implant formed by the cell culture and tissue engineering functions of the invention.

According to another aspect of the invention is a tissue implant produced within a bioreactor of the present invention.

According to yet another aspect of the present invention is a tissue implant produced by the tissue engineering system of the present invention.

According to another aspect of the present invention is a tissue engineered implantable construct for repair of bone trauma wherein the implant comprises a porous scaffold of a bone biomaterial in combination with active bone cells and tissue engineered mineralized matrix.

According to another aspect of the present invention is a tissue engineered implant comprising:

a cartilage zone comprising tissue engineered cartilage that is devoid of any mineral-based scaffold;

a bone biomaterial zone comprising a porous scaffold; and an interfacial zone between said cartilage zone and said bone biomaterial zone.

The cartilage zone promotes lateral integration with the host cartilage while the bone biomaterial zone promotes lateral and vertical integration with the subchondral bone plate when implanted in vivo. The interfacial zone provides the structural union between the cartilage zone and the bone biomaterial zone. The cartilage zone may additionally incorporate a secondary non-mineral scaffold that assists with the formation of tissue engineered cartilage and allows for the development of a shaped surface profile in keeping with the particular anatomical characteristics present at the site of implantation.

According to another aspect of the present invention is a method for digesting a tissue biopsy, the method comprising;

loading a tissue biopsy within a bioreactor connected with a media reservoir and flow system, said bioreactor having one or more sensors to detect physiological conditions within said bioreactor to a microprocessor providing tissue digestion enzymes; and monitoring and maintaining suitable digestion conditions within said bioreactor for a sufficient period of time for a desired level of tissue digestion.

According to another aspect of the present invention is a method for the proliferation of cells, said method comprising;

seeding cells onto a proliferation substrate or scaffold supported within a bioreactor connected with a media reservoir and flow system, said bioreactor having one or more sensors to detect physiological conditions within said bioreactor to a microprocessor; and monitoring and maintaining suitable culturing conditions within said bioreactor for a sufficient period of time for a desired level of cell proliferation.

According to another aspect of the present invention is a method for the differentiation of cells, said method comprising;

seeding cells onto a differentiation substrate or scaffold supported within a bioreactor connected with a media reservoir and flow system, said bioreactor having one or more sensors to detect physiological conditions within said bioreactor to a microprocessor; and monitoring and maintaining suitable culturing conditions within said bioreactor for a sufficient period of time for a desired level of cell differentiation.

According to another aspect of the present invention is a method for digesting a tissue biopsy to provide primary cells, including precursor cells such as stem cells, and then proliferating and differentiating the cells to enable the formation of a tissue implant, the method comprising;

loading a tissue biopsy within a bioreactor connected with a media reservoir and flow system, said bioreactor having one or more sensors to detect and relay physiological conditions within said bioreactor to a microprocessor;

providing tissue digestion enzymes;

monitoring and maintaining suitable digestion conditions within said bioreactor for a sufficient period of time to obtain disassociated cells;

seeding the disassociated cells onto a proliferation substrate or scaffold supported within a bioreactor connected with a media reservoir and flow system, said bioreactor having one or more sensors to detect physiological conditions within said bioreactor to a microprocessor;

monitoring and maintaining suitable culturing conditions within said bioreactor for a sufficient period of time to obtain the desired level of cell proliferation and expansion;

releasing the expanded cells from the proliferation substrate or scaffold;

seeding the expanded cells onto a differentiation substrate or scaffold supported within a bioreactor connected with a media reservoir and flow system, said bioreactor having one or more sensors to detect and relay physiological conditions within said bioreactor to a microprocessor; and monitoring and maintaining suitable culturing conditions within said bioreactor for a sufficient period of time to obtain a tissue implant.

According to another aspect of the present invention is a method for providing a skeletal implant, the method comprising;

seeding osteogenic and/or osteoprogenitor cells onto a porous scaffold of a bone biomaterial supported within a bioreactor connected with a media reservoir and flow system, said bioreactor having one or more sensors to detect physiological conditions within said bioreactor to a microprocessor; and monitoring and maintaining suitable conditions within said bioreactor for a sufficient period of time to allow the osteogenic and/or osteoprogenitor cells to proliferate and/or differentiate throughout the scaffold to provide a tissue implant for orthopedic applications.

According to still another aspect of the invention is a method for providing a cartilage implant, the method comprising;

seeding chondrogenic and/or chondroprogenitor cells onto a porous scaffold of a biomaterial supported within a bioreactor connected with a media reservoir and flow system, said bioreactor having one or more sensors to detect physiological conditions within said bioreactor to a microprocessor; and monitoring and maintaining suitable conditions within said bioreactor for a sufficient period of time to allow the chondrogenic and/or chondroprogenitor cells to proliferate and/or differentiate throughout the scaffold to provide a cartilage implant.

According to still another aspect of the invention is a method for washing cells, the method comprising:

loading a cell suspension containing one or more undesired chemicals into a chamber;

continuously recirculating the cell suspension from the chamber through a cross-flow filtration module that comprises a membrane impermeable to said cells but permeable to said undesired chemicals to provide a washed cell suspension; and collecting the washed cell suspension.

According to yet another aspect of the invention is a method for enrichment of cells, the method comprising:

loading a cell suspension containing excessive cell suspension volume into a chamber;

continuously recirculating the cell suspension from the chamber through a cross-flow filtration module that comprises a membrane impermeable to the cells but allowing the excessive cell suspension volume to be removed and collected.

According to yet another aspect of the invention is a method for providing an implant for re-establishing the inner nucleus of a spinal disc, the method comprising;

seeding nucleus pulposus cells within a scaffold a porous scaffold of a biomaterial supported within a bioreactor connected with a media reservoir and flow system, said bioreactor having one or more sensors to detect physiological conditions within said bioreactor to a microprocessor; and monitoring and maintaining suitable conditions within said bioreactor for a sufficient period of time to allow proliferation and/or differentiation of the nucleus pulposus cells and the expression of extracellular matrix components characteristic of the nucleus pulposus.

According to still a further aspect of the present invention is a method for the preparation of quality assessment samples for use in clinical tissue engineering, said method comprising;

parallel preparation of primary and secondary implants using the system of the invention as described herein, where the primary implant is for implantation and one or more secondary implants are for testing purposes to infer the calibre of the primary implant.

The tissue engineering system of the present invention in various embodiments is under the control of one or more microprocessors that may be preprogrammed in order that the user can select a specific type of environment (or sequence of environments) within the bioreactor such as tissue digestion, cell proliferation, cell differentiation and/or tissue construct formation. This eliminates operator intervention and reduces the possibility of inadvertent contamination.

The tissue engineering system of the invention can be provided as a "kit". In this manner the device, tissue engineering module(s), bioreactor(s) and various components thereof can be packaged and sold together along with instructions and quality control techniques.

The system of the present invention is ideal for clinical use in hospitals, and in particular surgical settings where due to trauma and/or disease, a tissue-engineered implant is desired. Using the present system, tissue engineered implantable constructs can be safely prepared from autologous tissue obtained via patient biopsy, allogenic cells or xenogenic cells. The specifications of such tissue engineered implantable constructs can be matched to the type, size and condition of the implantation site. Furthermore, the implant as generated by the present system contains active cells that promote integration with the host thereby improving patient recovery.

In practice, using an autologous cell model, a tissue biopsy can be obtained from the patient and placed directly into the bioreactor present on the tissue engineering module while in the operating room. A specific bioreactor design is selected depending on the type and size of the tissue construct desired. At the completion of the tissue engineering process, the tissue construct produced can be transported still contained in the sterile bioreactor to the operating room for implantation back into the patient. The system is ideal for providing "customized" autologous tissue implants in a safe and therapeutically effective manner.

The system and methods of the present invention are not limited to providing automated cell culture techniques. The tissue engineering system described moves well beyond the cell expansion used in cell therapy. The tissue engineering system may be used to create functional tissue constructs where the cells present are active, differentiated and already expressing extracellular matrix. Consequently, the tissue constructs so produced are in a high state of development and thereby accelerate the rate and improve the quality of tissue repair at the implant site.

The system of the invention is also suitable for pharmacological research. Specifically, the system finds use in the area of drug development. New potential drugs and molecules can be tested on cells and tissues to determine effects on cellular events and tissue development. Such testing can be done on a patients own cells/tissues to assess and possibly avoid adverse side effects prior to administration. Alternatively, specialized cell lines or tissues can be used with the system as a key tool in the drug discovery process. The system can be programmed to monitor and assess various physiological conditions of the cells/tissues present within the bioreactor and thus provide a fast indication of the biological effects of a selected drug or molecule.

The system may also be used for research and development studies where conventional tissue engineering techniques are difficult to use and practice, and/or in conditions requiring extensive diagnostic recording. For example, microgravity studies involving tissue engineering are difficult to conduct due to the unique properties of this environment. Traditional cell and tissue culture techniques are simply not viable in this environment due to fluid containment issues and the absence of gravity-based transport of cells. The system and methods of the invention are easily adaptable to the microgravity environment as the system is completely sealed to prevent fluid loss and the migration of cells as part of the tissue engineering process can be achieved by controlled fluid flow.

Other features and advantages of the present invention will become apparent from the following detailed description, examples and drawings. It should be understood, however, that the detailed description, specific examples and drawings while indicating embodiments of the invention are given by way of illustration only, since various changes and modifications within the spirit and scope of the invention will become apparent to those skilled in the art from said detailed description.

BRIEF DESCRIPTION OF THE DRAWINGS

The present invention will be further understood from the following description with reference to the figures, in which:

FIG. 7(a) shows an enlarged perspective view of the bioreactor and pump unit;

FIG. 7 (b) shows an enlarged perspective view of the pump unit and the associated pump tubing;

FIG. 23 shows a further embodiment of the tissue engineering module with separate bioreactors for tissue digestion/cell collection, cell proliferation, and cell differentiation/tissue formation.

DETAILED DESCRIPTION OF THE INVENTION

The present invention is directed to an integrated, automated tissue engineering device for the ex vivo processing of cells, particularly autologous cells, to enable cell proliferation, cell differentiation and tissue formation in an efficient and consistent manner requiring minimal human intervention. The tissue constructs developed within the device may be integrated into a host to assist in tissue reconstruction procedures and subsequent patient recovery. Furthermore, the invention provides automated methods for tissue engineering using a variety of cells from a number of different sources (for example autologous cells obtained via patient biopsy, allogenic cells or xenogenic cells). Furthermore, the cells may be precursor cells, primary cells, cells from an immortal cell line and combinations thereof.

Figure 1:
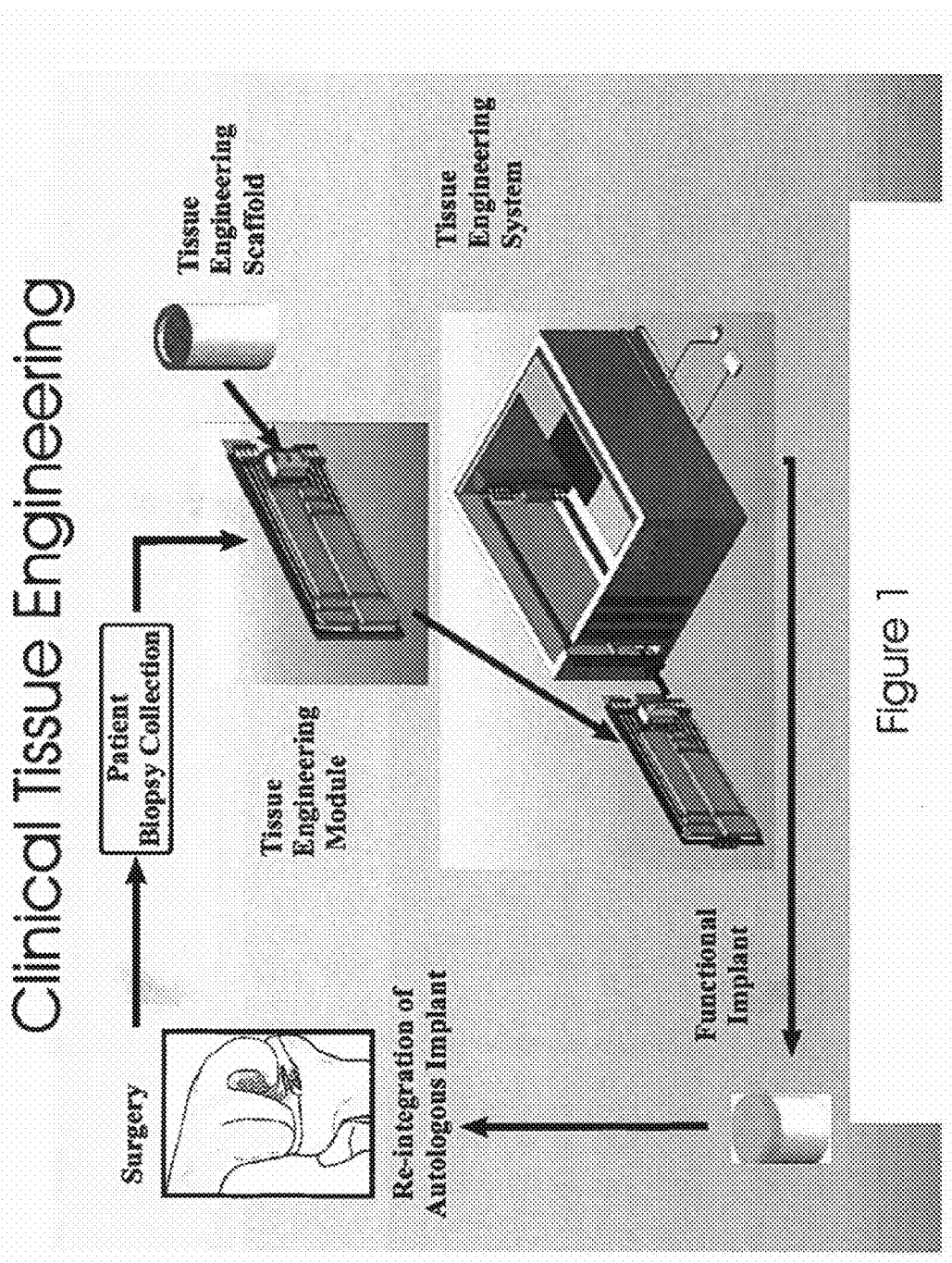
FIG. 1 illustrates a general methodology for clinical tissue engineering as applied to the example of cartilage repair using autologous chondrocytes.

The general methodology and principle for clinical tissue engineering incorporating the tissue engineering system and methods of the present invention is illustrated in FIG. 1, using autologous cartilage tissue engineering as a representative example. In such example, cells (i.e. chondrocytes) are obtained from a surgical biopsy of a patient and either manually or automatically seeded onto a suitable substrate or scaffold (i.e. a Skelite™ support). The chondrocytes and the support are present within the bioreactor portion of an automated tissue engineering module, with the module forming part of a clinical base station of the tissue engineering system. A central microprocessor is present within the tissue engineering system and controls and customizes the internal environment of the bioreactor, and hence facilitates tissue growth therein, resulting in the stimulation of cell growth within and onto the support to generate an implant. Sensors within the bioreactor provide feedback to the microprocessor to ensure that the cells are seeded, expanded and differentiated in a desired and controlled manner to provide an autologous tissue implant. Once the implant is generated, it is removed from the bioreactor for surgical implantation into the patient. The present system provides an advantageous way to provide autologous tissue engineered implants in a sterile, safe, convenient and efficacious manner. Furthermore, the ability to prepare tissue engineered implants in a clinical setting allows considerable flexibility in the locations for undertaking the tissue engineering process. While the system can be used in a centralized location, the design and operation of the system enables clinical use at regional centers. Such widespread availability precludes the transportation of biological material to and from centralized cell/tissue processing facilities, thereby improving the cost effectiveness and efficiency of the tissue engineering process while avoiding shipment, tracking and regulatory complications.

Figure 2:
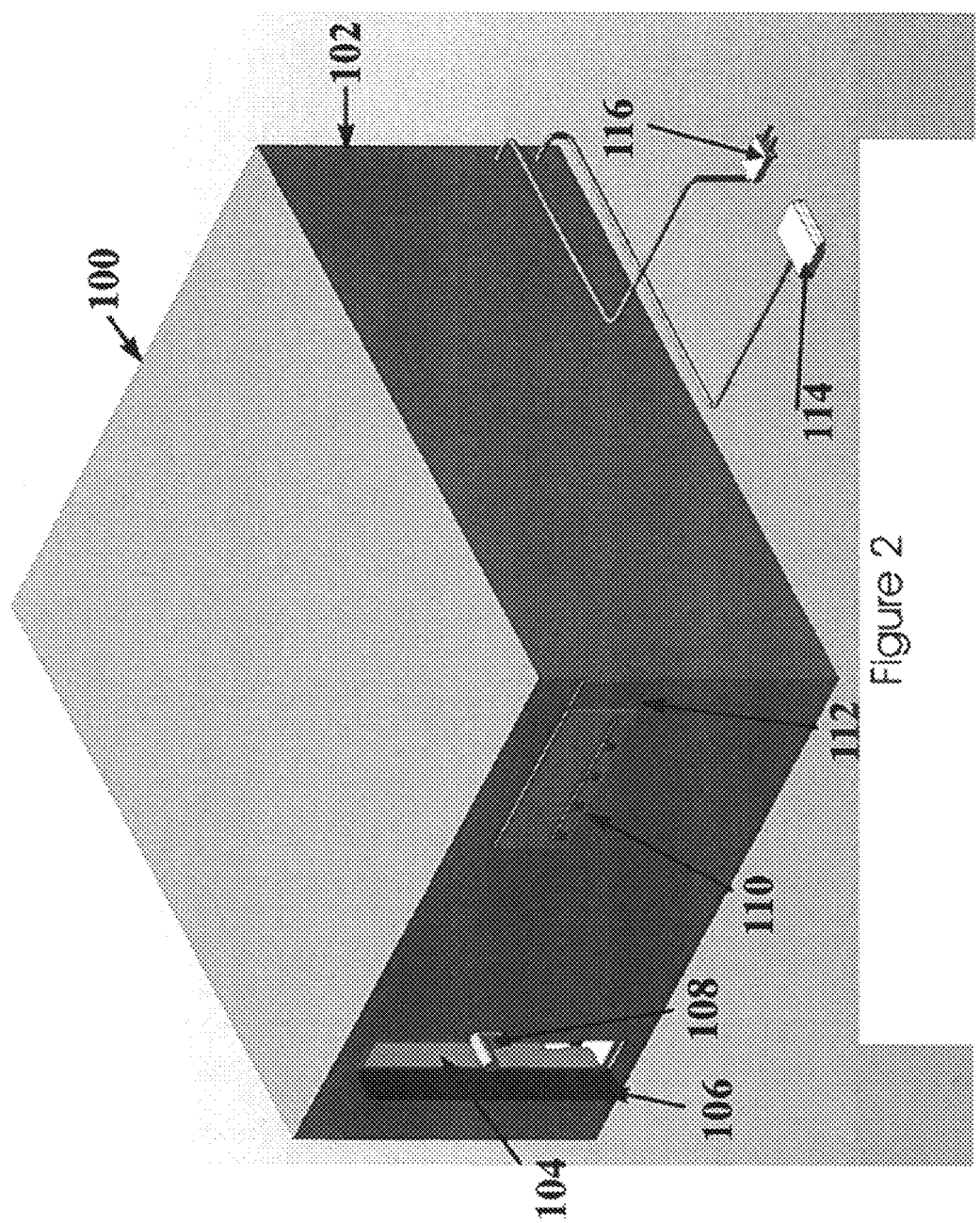
FIG. 2 shows an integrated tissue engineering device of the present invention.
Figure 3:
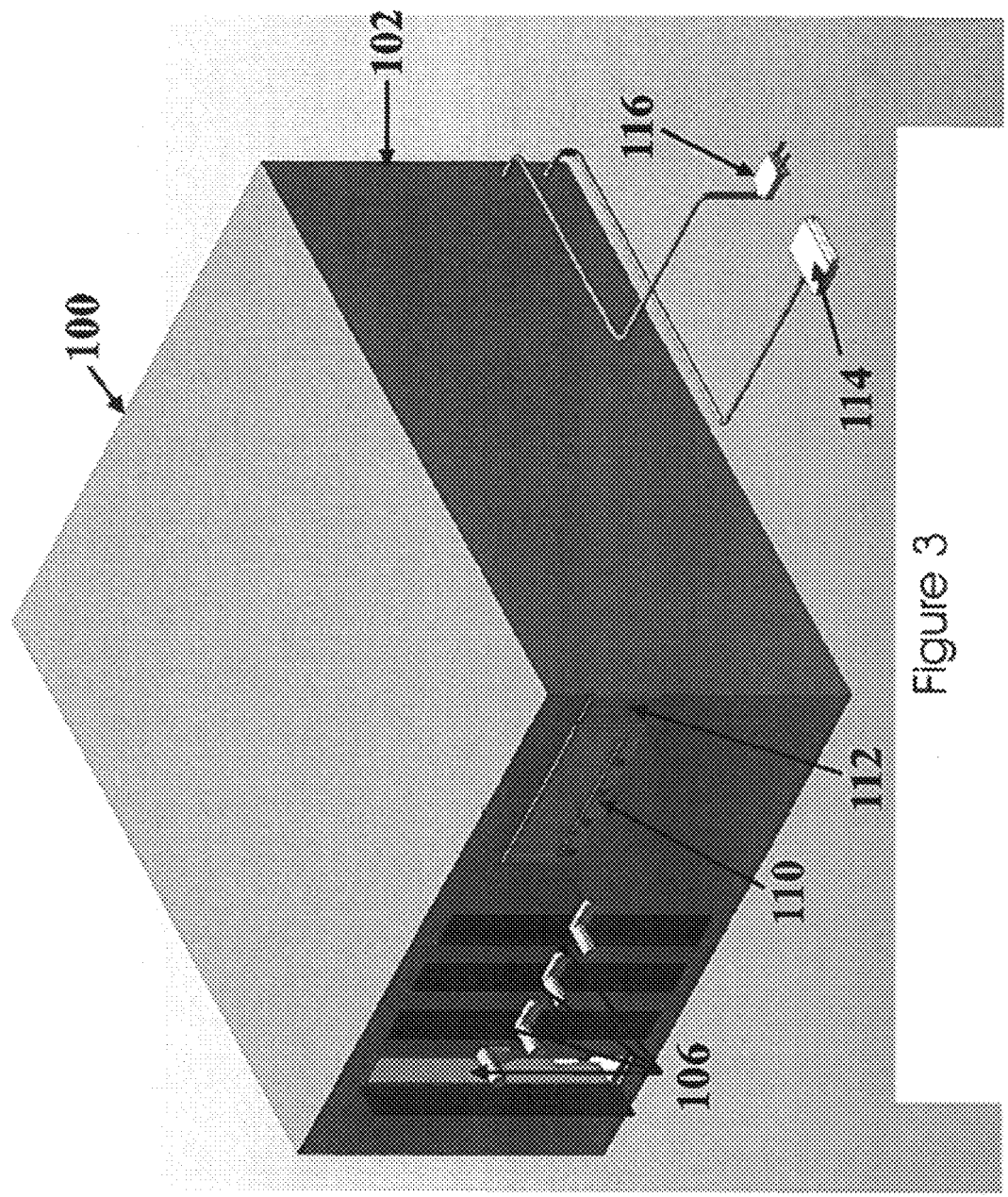
FIG. 3 shows a further embodiment of the tissue engineering device of FIG. 2.
Figure 4:
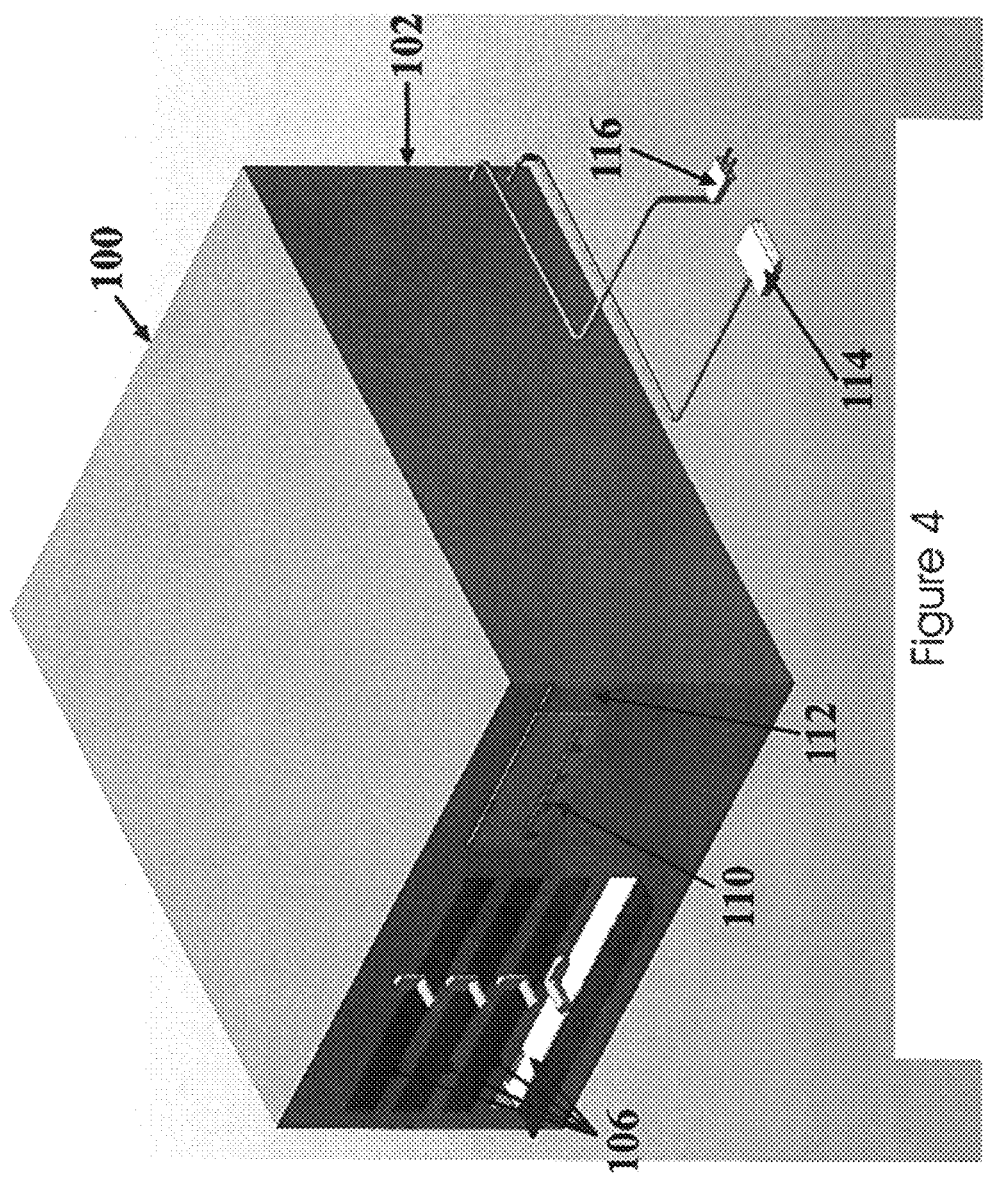
FIG. 4 shows a further embodiment of the tissue engineering device of FIG. 2.

In accordance with an embodiment of the present invention is a tissue engineering system as shown in FIG. 2 and generally indicated with reference numeral 100. The system 100 (may alternatively be referred to as a device) comprises a housing 102 having an insertion slot 104 for receiving a tissue engineering module. The insertion slot 104 has a movable door 106 and a locking mechanism 108. A user interface 110 such as a touch screen, key pad or combination of both is provided for control of system operation and for the display of system status. A data storage system 112 is present which permits the recording of information via a variety of mediums known to those of skill in the art (i.e. ZIP, CDROM, diskette, flashcard). A computer/communications link 114 provides the capability to upload new software, modify control parameters using an external computer, download data as well as troubleshoot and test the device. This link also permits the system to be connected to electronic information systems present at the clinic. The system 100 is powered with a power input 116. FIG. 3 shows a further embodiment of the system 100 having several bay doors 106 to accommodate several tissue engineering modules. FIG. 4 shows a further embodiment of the system 100 having bay doors 106 orientated in a horizontal manner to allow for the preferential orientation of the tissue engineering module relative to the gravity vector.

Figure 5:
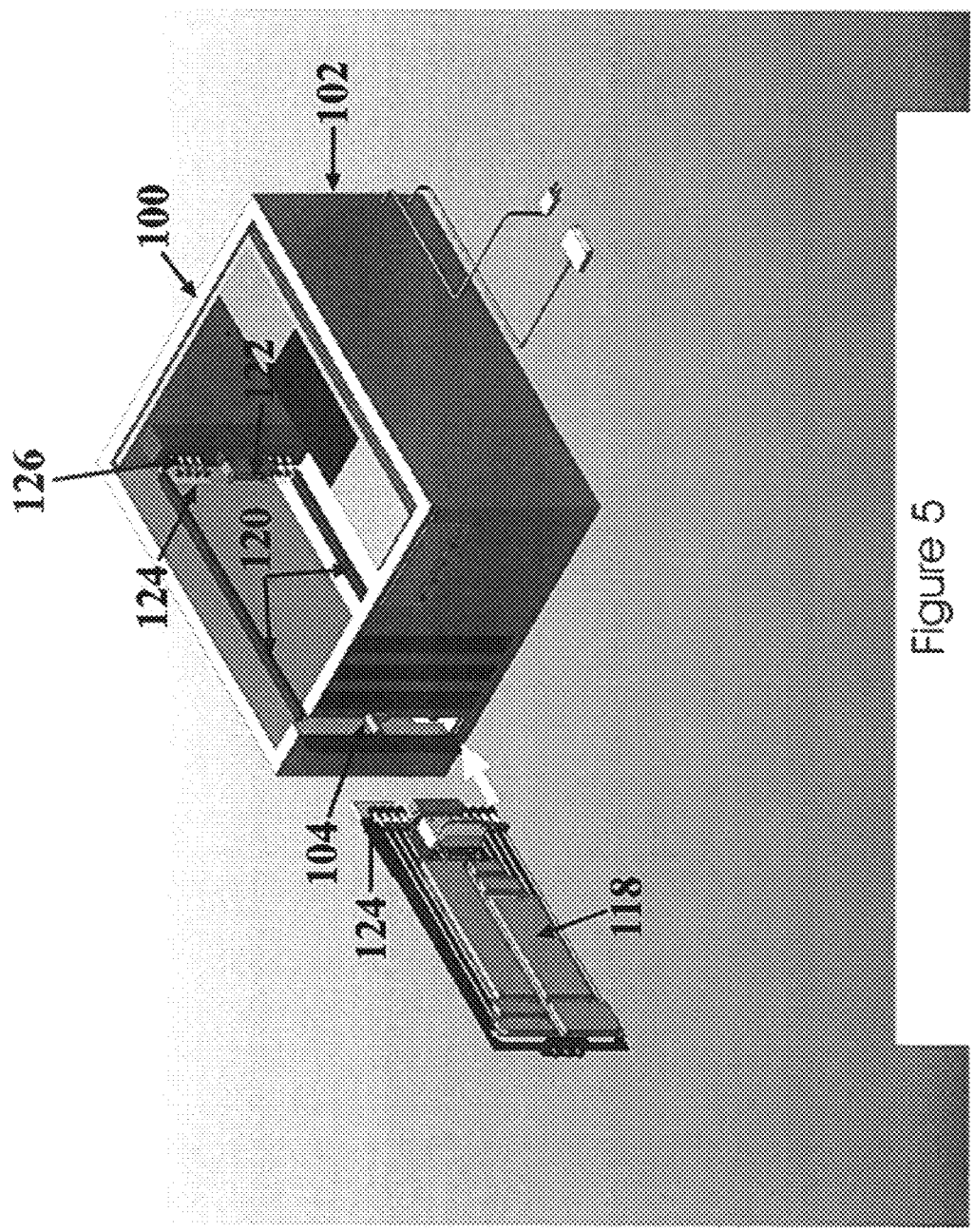
FIG. 5 shows a cut-away view of the tissue engineering device of FIG. 2 illustrating some of the internal components and a tissue engineering module for insertion into the device.

FIG. 5 shows the internal configuration of the system 100 represented in FIGS. 2 and 3 with the vertical orientation of the bay doors for vertical insertion of a tissue engineering module. A tissue engineering module 118 is shown for insertion within the insertion slot 104 of the bay door 106. The tissue engineering module 118 slides into the system housing 102 via a guide rail system 120. Upon insertion, the module 118 engages with one or more pump units 122 (i.e. peristaltic, piston, diaphragm or rotary), electrical connectors 124 (i.e. DIN, AMP, PCB, breadboard socket), and valve actuators 126 (i.e. servo motor, linear drive, linear actuator). Any suitable guide system to allow the module to be inserted properly into the system may be contemplated as is understood by one of skill in the art.

Figure 6:
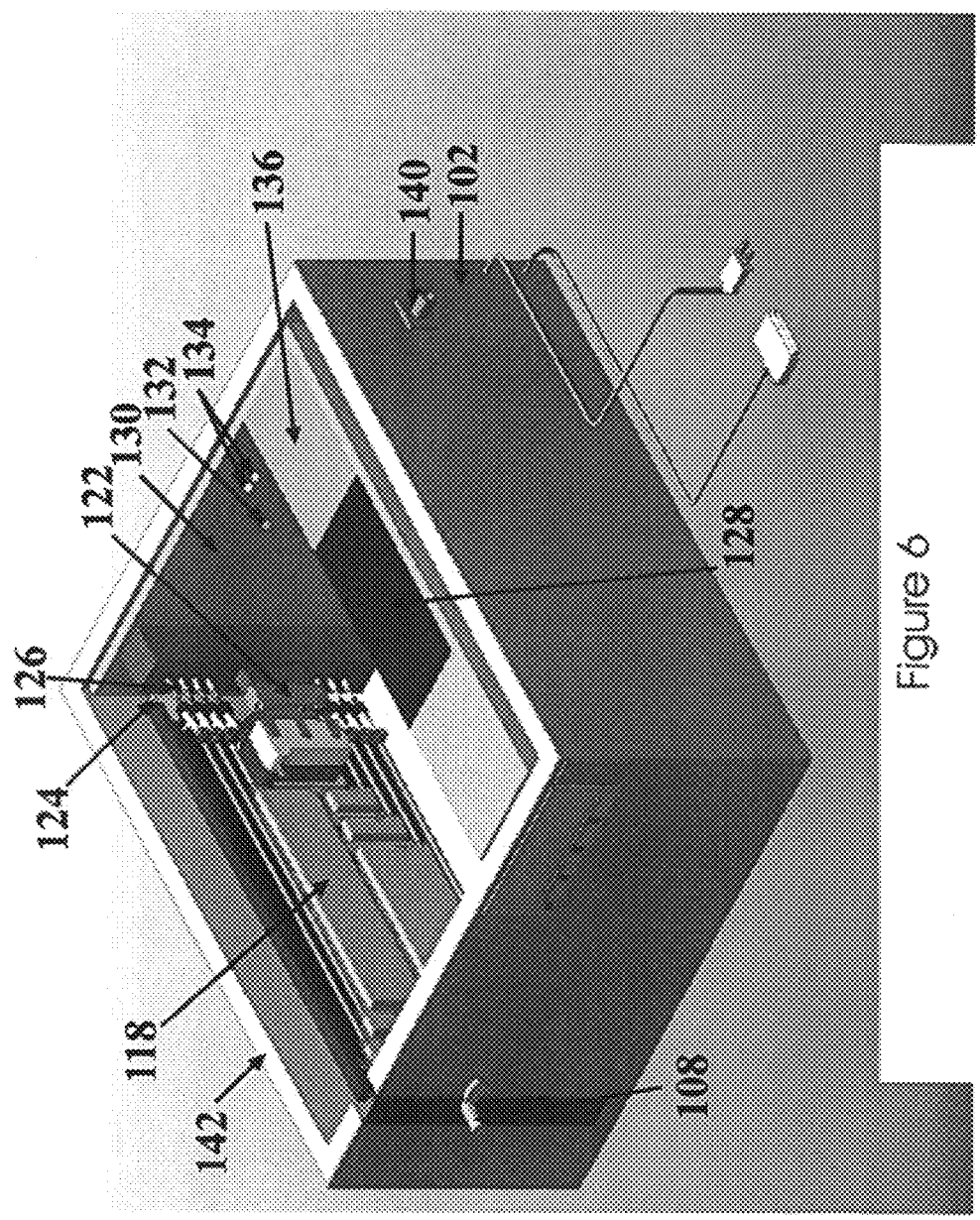
FIG. 6 shows an enlarged cut-away view of the tissue engineering device of FIG. 2 illustrating an inserted tissue engineering module.

As better seen in FIG. 6, where the tissue engineering module 118 is inserted into the housing 102, a series of valve actuators 126 interface with valves (shown in more detail in FIGS. 7 and 7a) on the module to provide flow control. The electrical connectors 124 provide electrical connection between the module 118 and a central microprocessor unit (CPU) 128 via an electronic back-plane 130. The CPU 128 controls the operational sequence, the transport of fluids and gases, the management of process data, the monitoring of system status, the user interface, and the external data communication port. The CPU 128 provides control through electrical links with active and passive electrical components present on the back-plane 130 and each of the inserted tissue engineering modules 118.

Temperature sensors 132 (I.e. thermocouple, RTD or thermistor), gas sensors 134 (i.e. $O_2$ and $CO_2$) and an environment control unit (ECU) 136 are controlled by the CPU 128 to maintain the environment (i.e. temperature and gas atmosphere) within the housing 102 using standard methods known to those skilled in the art. The environment can be adjusted to meet the requirements of the tissue engineering process, including storage of reagents at refrigeration temperature (i.e. 4° C.), the simulation of nominal body temperature (i.e. 37° C.), and the availability of gaseous mixtures for transport into and out of the module 118 in the event that the module is equipped with gas exchange components (i.e. membranes). Gaseous conditions are monitored by the gas sensors 134 located within the housing 102 and the data is sent to the CPU 128 via the electronic back-plane 130. Gas input(s) to the ECU can be via gas supply inlet 140 provided within the housing 102 configured with standard fittings. In other embodiments, gases may be housed within the ECU. Gases for use within the device include but are not limited to oxygen, carbon dioxide, nitrogen and mixtures thereof. In order to adequately contain such gases within the housing 102, the bay door 106 is configured to provide for a hermetic seal when closed. The housing 102 is insulated with insulating material 142 such as styrofoam, aerogel, fiberglass and the like to allow for the efficient regulation of internal temperatures (i.e. 4° C. to 37° C.).

While the tissue engineering system of the present invention is generally shown to comprise a boxed shaped housing, it is understood by one of skill in the art that the housing may be made of various configurations so long as it may accommodate the components as described herein. For example, this includes but is not limited to open configurations that may not require a top and/or side portions.

Figure 7:
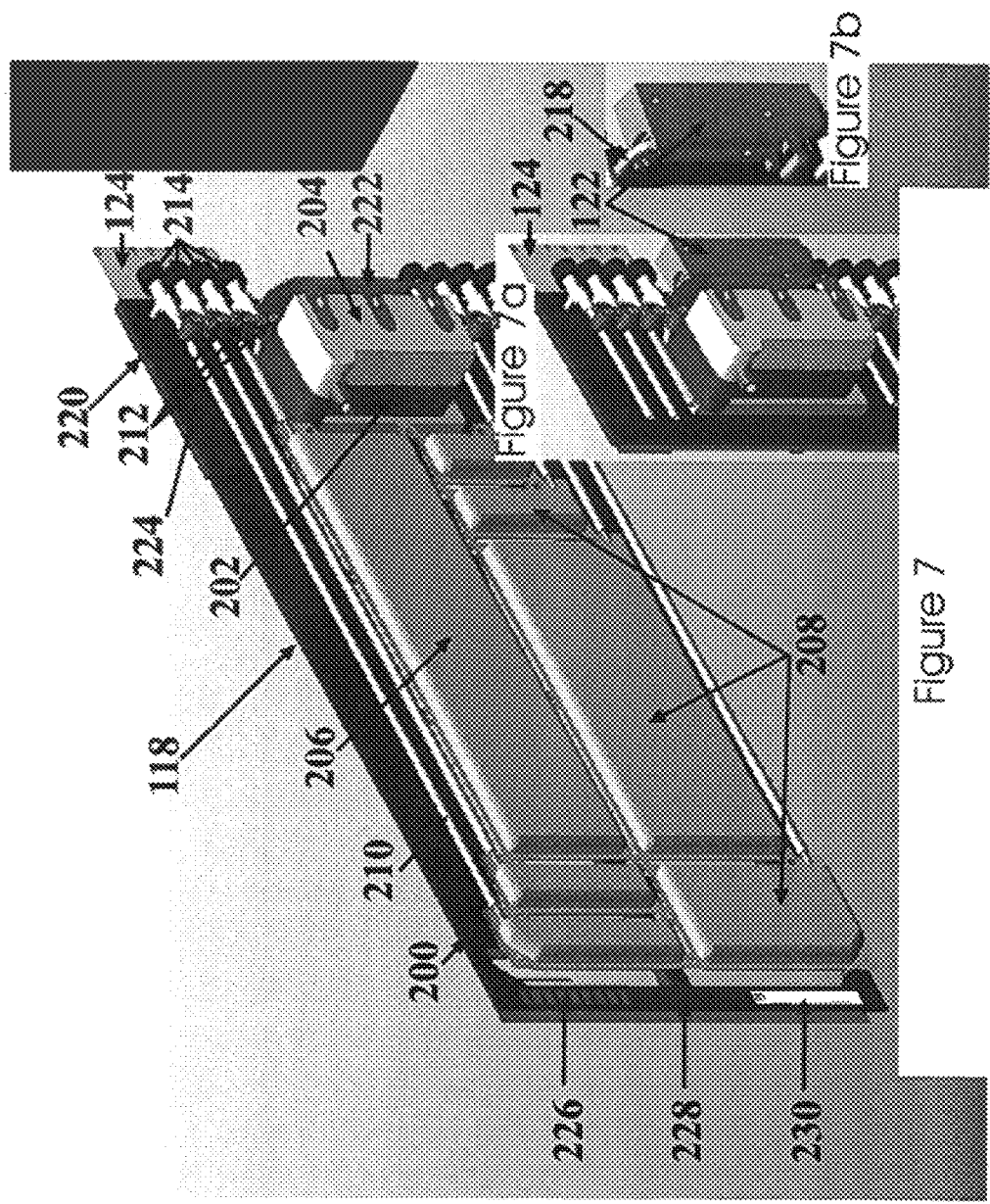
FIG. 7 shows an enlarged perspective view of the tissue engineering module and interface with components of the device housing.
Figure 8:
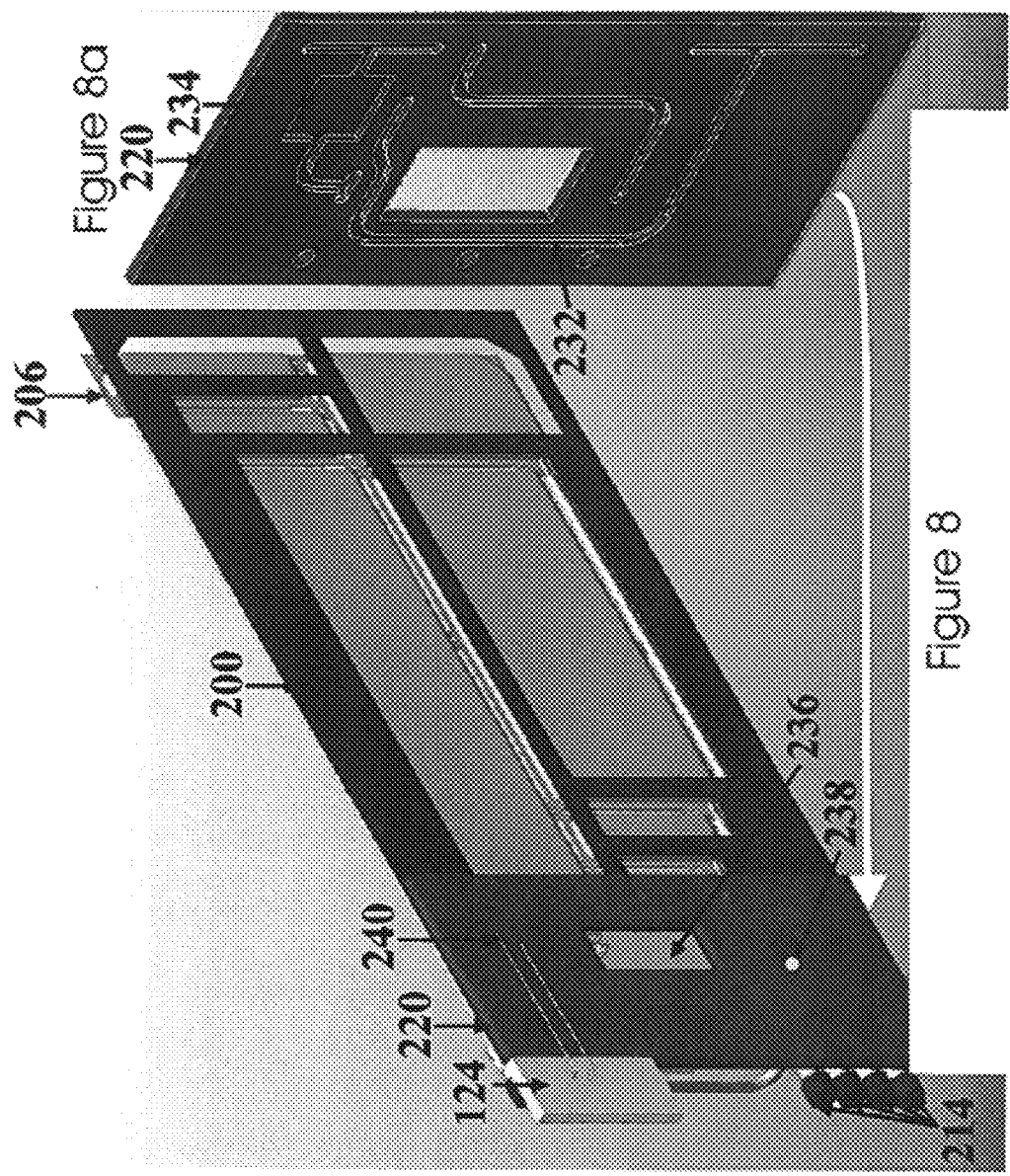
FIG. 8 shows a perspective view of the reverse side of the tissue engineering module of FIG. 7 and the internal configuration of the flow plate that attaches thereto.
Figure 9:
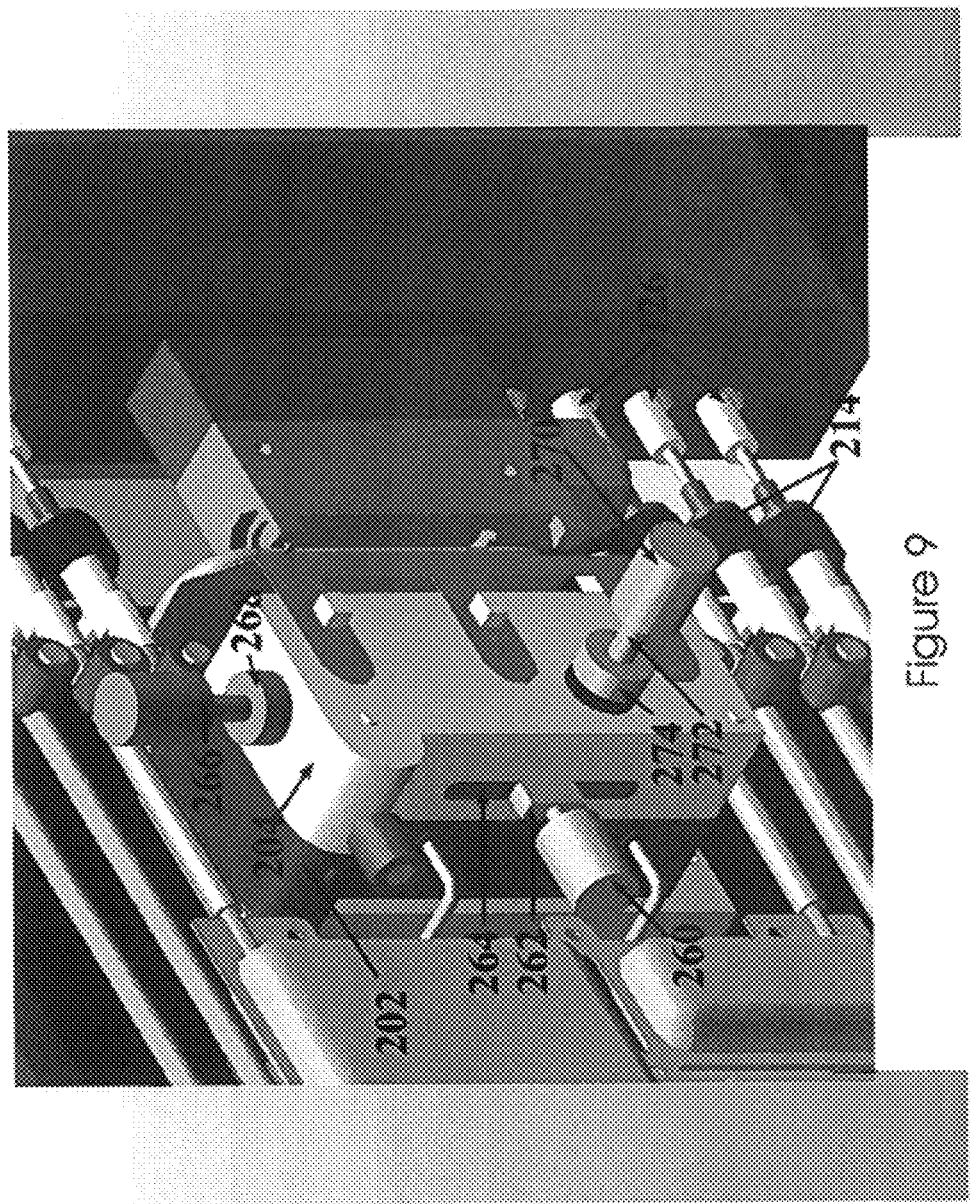
FIG. 9 shows an enlarged perspective view of the mixing and micro-loading components associated with the instrumented bioreactor design.

The tissue engineering module 118 is illustrated in more detail in FIGS. 7-9. The tissue engineering module 118 comprises a rigid structural spine 200 to which is affixed a bioreactor 202. The bioreactor 202 comprises a bioreactor housing that has a lid 204 and may be customized with respect to the substrate(s) or scaffold(s) contained therein to enable tissue digestion, cell culture, cell proliferation, cell differentiation, tissue implant formation and combinations thereof. The bioreactor lid may be detachable or alternatively made integral to the bioreactor housing. The bioreactor 202 may be separately detachable and disposable relative to the structural spine 200. To enable such detachment, the bioreactor 202 and the structural spine 200 may use fluid disconnect fittings that include the provision for self sealing of input and output lines to avoid loss of fluids and to prevent contamination of the contents of the bioreactor. The entire tissue engineering module may be considered to be disposable following the completion of a tissue engineering sequence, as this practice prevents contamination arising from prior use. Alternately, only selected components of the module 118 may be considered as disposable due to contact with fluids, leaving non-contamination prone components available for re-use.

As seen in FIGS. 7, 7a and 7b, a fluid containment system 206 is affixed onto the structural spine 200 of the tissue engineering module 118. The fluid containment system 206 is comprised of a sterile series of flexible reservoirs 208 and flexible tubing 210 for supplying and retrieving types of tissue and cell culture fluids and pharmaceuticals to and from the bioreactor 202. The reservoirs 208 may be of varying configuration and number as required and may contain different types of cell and tissue culture media, growth factors, pharmaceutical agents and may also contain waste media and/or media samples from the bioreactor 202. Fluids are loaded or removed from the fluid containment system 206 via a series of fluid access ports 212. Tubing 210 is present to provide fluid connection between the various reservoirs 208 and the fluid control components, such as the fluid flow control valves 214. The fluid flow control valves 214 are opened and closed by valve actuators 126. Similarly, the pump unit 122 interfaces with disposable pump components present on the module. These pump components may be pistons, diaphragms, rotary elements or peristaltic tubing 218, provided that the operation of these components does not generate harsh conditions, such as excessive shear stress, that compromise cell viability during the transfer of cell suspensions. The pump unit 122 and the valve actuators 126 reside within the housing 102. Alternately, the actuators and pump unit may form part of the tissue engineering module, however, this may result in disposal of these components following patient use. Fluid is transferred out of the reservoirs 208 by the programmed action of the pump unit 122 on the pump tubing 218. Fluid travels from a flexible fluid reservoir 208 to a fluid valve 214 via tubing 210. A fluid flow plate 220 (as shown in FIG. 8) directs fluid flow between different flow control valves 214 and the pump tubing 218 of the pump unit 122. Fluid is returned to a selected empty reservoir 208 for storage. A flexible printed circuit board (PCB) 222 provides the electronic interface for electronic components (i.e. sensors) present on the structural spine 200 and/or the bioreactor 202. In the event that a sensor indicates that a monitored parameter (e.g., pH) is outside acceptable levels, the CPU triggers a control intervention such as replacing the media within the bioreactor.

The tissue engineering module may optionally include a microprocessor 224 to enable data processing and data storage directly on the module. This information may transferred to the central CPU 128 while the module is inserted into the housing 102 and retained in electronic memory for later access once the module is removed. In addition to the data stored via the microprocessor or memory chip resident on the tissue engineering module, the module may also optionally include a bar code 226, magnetic strip 228, electronic memory (not shown) and/or ID label 230 to facilitate administrative tracking within the clinic.

As seen in FIG. 8, the fluid flow plate 220 is secured to the structural spine 200 of the tissue engineering module 118. The technique for attachment of the fluid flow plate may be, but is not limited to, a press fit, snap fit, ultrasonic weld, solvent bond and the like, recognizing that the technique adopted must allow for sealing of the assembly to avoid loss of fluids and to prevent contamination. As shown in the disassembled view in FIG. 8a, the fluid flow plate 220 has an integral fluid pathway 232 to provide a means for directing flow associated with the actuation of the fluid valves 214. New flow paths may be accommodated via revisions to the pathway present on the flow plate 220. In one embodiment, the fluid plate 220 may be integrally formed into the structural spine 200 to form a single component. A fluid heating and mixing chamber 234 is included to ensure fluids that are directed to the bioreactor are at the correct temperature and are adequately mixed so as to not disrupt the biological processes underway in the bioreactor. Furthermore, a thermoelectric element 236 is present on the tissue engineering module 118 to vary the temperature within the bioreactor 202 compared with the operational temperature of the module, as defined by the operation of the ECU 136. Such a temperature change may be necessary to simulate nominal physiological conditions within the bioreactor, while the remaining components of the tissue engineering module, particularly the reagents and/or samples, are at a reduced temperature (i.e. refrigeration) to maintain physical, chemical and/or biological viability. Power and control of the thermoelectric element is performed by the CPU 128. In addition to sensors present on the bioreactor, a sensor 238 present on the tissue engineering module provides feedback to the CPU 128. The sensor and thermoelectric connections are made via the electrical cabling 240 and connector 124.

FIG. 9 shows the mixing and micro-loading aspects of the tissue engineering module 118. The bioreactor 202 has a mixing drive 260 operably connected with a mixing actuator 262 and to the mixing diaphragm 264. The mixing diaphragm is incorporated as part of the bioreactor 202 or the bioreactor lid 204, as shown. In operation, the mixing drive 260 in combination with the mixing actuator 262 provide translation or pulsing of the mixing diaphragm to effect controlled mixing of the contents of the bioreactor 202. Ideally, the nature of the mixing is such to avoid high fluid shear that could compromise the physical integrity of cells present within the bioreactor. For certain tissue engineering protocols, moderate levels of fluid shear are actually beneficial for the successful development of tissue constructs. In addition to the mixing components, an impact drive 266 and impact actuator 268 are present. These components serve to apply a controlled impact to the bioreactor assembly at the conclusion of the proliferation sequence to assist with the release of cells from a proliferation substrate or scaffold resident within the bioreactor. Also provided is a micro-loading drive 270 in operable connection with a micro-loading actuator 272 and micro-loading diaphragm 274. The micro-loading diaphragm 274 is incorporated as part of the bioreactor 202 or the bioreactor lid 204, as shown. The location and orientation of the micro-loading diaphragm is such to enable intimate contact with the substrate or scaffold and any associated cells or tissues present in the bioreactor 202. The application of micro-loads is known to be advantageous for certain tissue engineering protocols. The mixing drive 260, impact drive 266, and micro-loading drive 270 may be any of a series of electromechanical devices such as solenoids, linear drives, rotational drives, or piezo electric components. Furthermore, it is possible for the mixing drive 260, impact drive 266, micro-loading drive 270, and the related actuators to be mounted on the housing 200. Alternatively, the drives and actuators may be mounted on the tissue engineering module or the bioreactor provided that the design of the drives is consistent with the disposable nature of the tissue engineering module. In addition to the provision of mechanical stimulation, the bioreactor may also be configured to introduce electrical and/or chemical stimulation of the tissue construct. In particular, electric fields may be generated in the region of the bioreactor to enhance cell transport and/or tissue formation. Methods of generation of electric fields are known to those of skill in the art and include but are not limited to the provision of electric coils.

Figure 10:
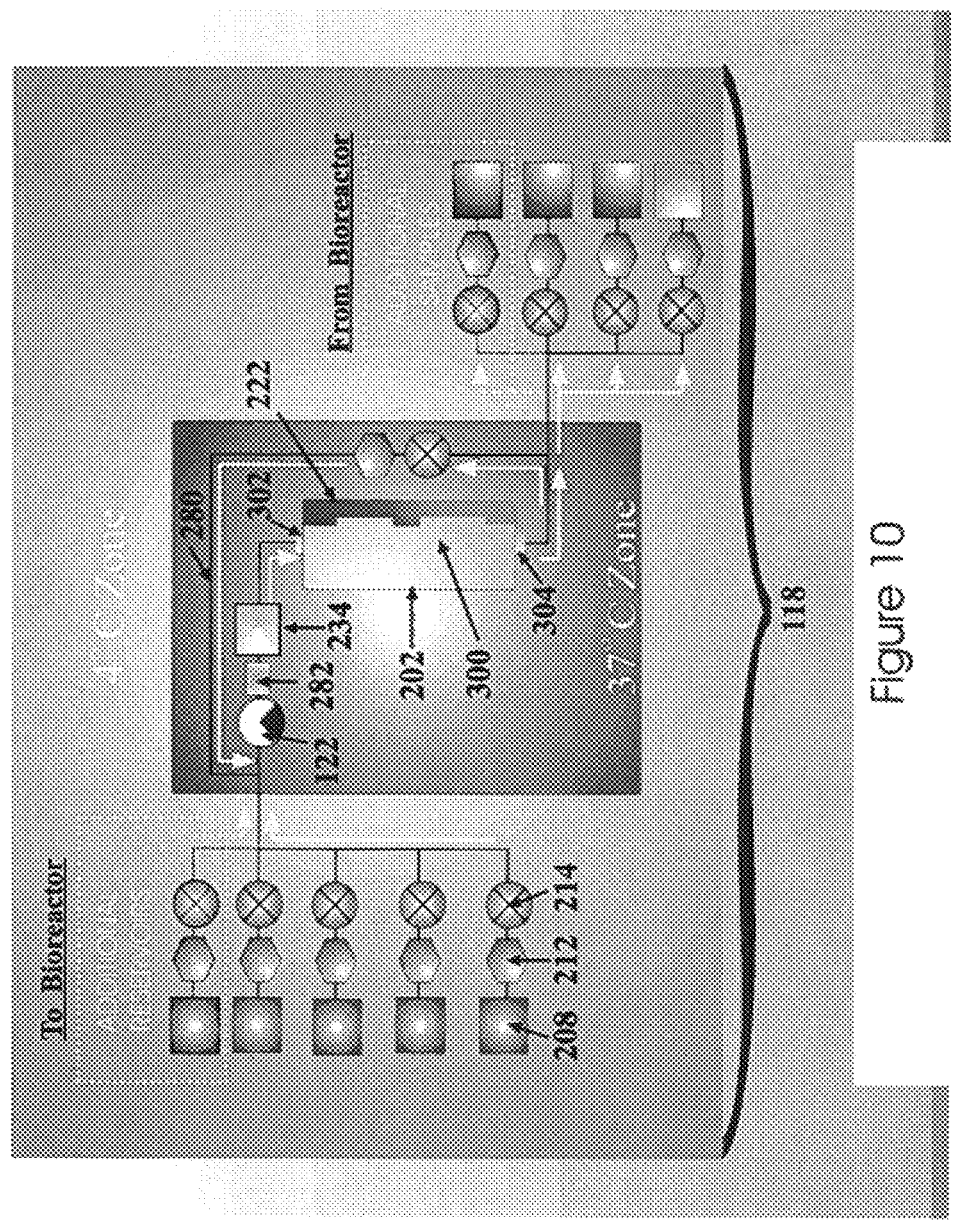
FIG. 10 shows the basic tissue engineering fluid flow schematic.
Figure 12:
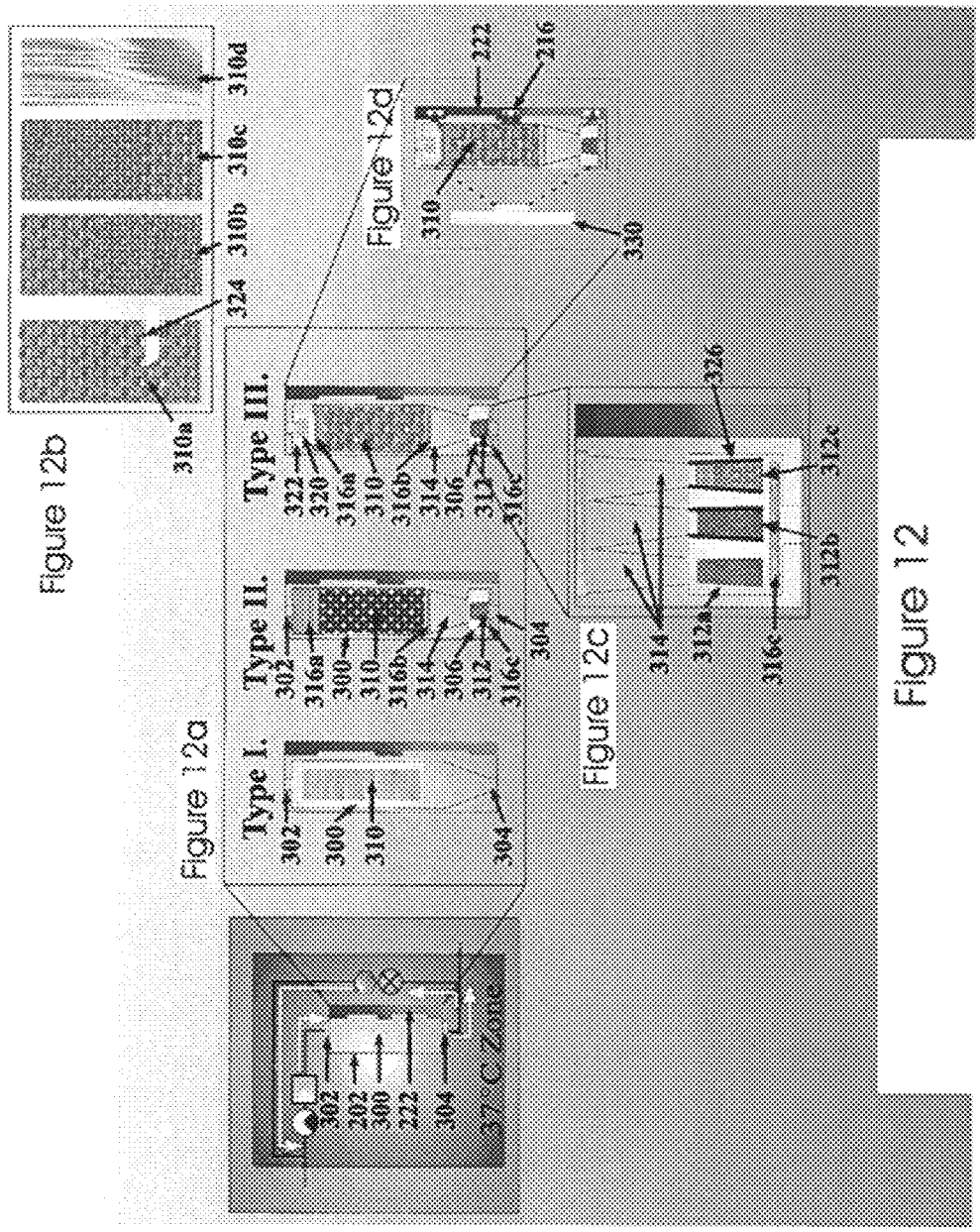
FIG. 12 shows alternate bioreactor, proliferation substrate or scaffold, differentiation scaffold and process monitoring designs, as applicable to different tissue engineering scenarios.
Figure 17:
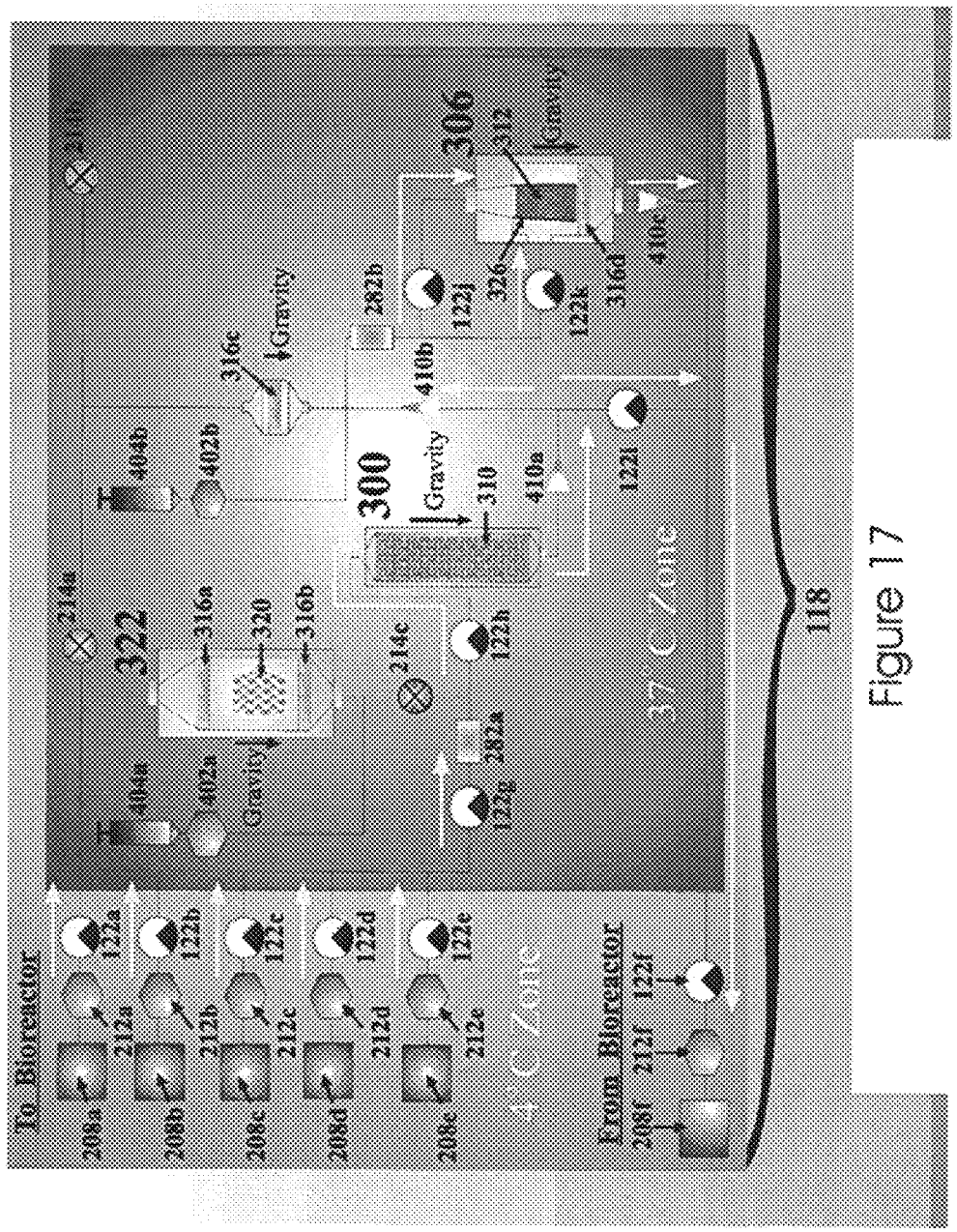
FIG. 17 shows a further embodiment of the tissue engineering fluid flow schematic.

FIG. 10 illustrates a basic fluid flow schematic for the tissue engineering module 118 in which there is a single cell or tissue culture chamber present within the bioreactor 202, (refer to descriptions of FIGS. 12 and 17 for further information on the multi-chamber bioreactors). The flow path links the bioreactor 202 to reservoirs 208 that supply fluid and collect waste. The fluid access ports 212 may be used to load reagents or remove samples or waste fluid. Flow is generated by the operation of pump unit 122 with flow direction defined by actuation of specific flow control valves 214. Perfusion to the bioreactor can be either continuous or pulsatile, provided that the associated flow does not result in high fluid shear in regions containing cells, as such conditions could damage the cells or an emerging tissue construct. A recirculation loop 280 is provided to allow the fluid contents of the bioreactor to be either monitored or modified by external components, such as an in-line gas exchange membrane 282, without necessitating the delivery of new fluid from the fluid reservoirs 208. Components of the tissue engineering module 118 dedicated to storing fluids, (i.e. reservoirs 208), are kept refrigerated at approximately 4° C. to facilitate storage of fluids that would otherwise degrade at the elevated temperatures used to simulate body temperature (i.e. 37° C.). According to a preprogrammed routine, the CPU 128 controls the operation of fluid valve(s) 214 to allow fluid stored in a reservoir 208 to be delivered via the pump unit 122 into a heating and mixing chamber 234 prior to entry into the bioreactor chamber 300 (shown in detail in FIGS. 13, 14 and 15). Fluids are supplied to the bioreactor via the inlet port 302 and removed via outlet port 304. To simulate normal body temperatures for optimal cell and tissue culture performance, the bioreactor 202, the pump unit 122 and the heating and mixing chamber 234 are maintained at approximately 37° C. by the operation of a thermoelectric element 236. It will be obvious to one skilled in the art that alternate thermal regulation devices may be used to obtain the desired thermal profiles for the tissue engineering module 118.

Figure 11:
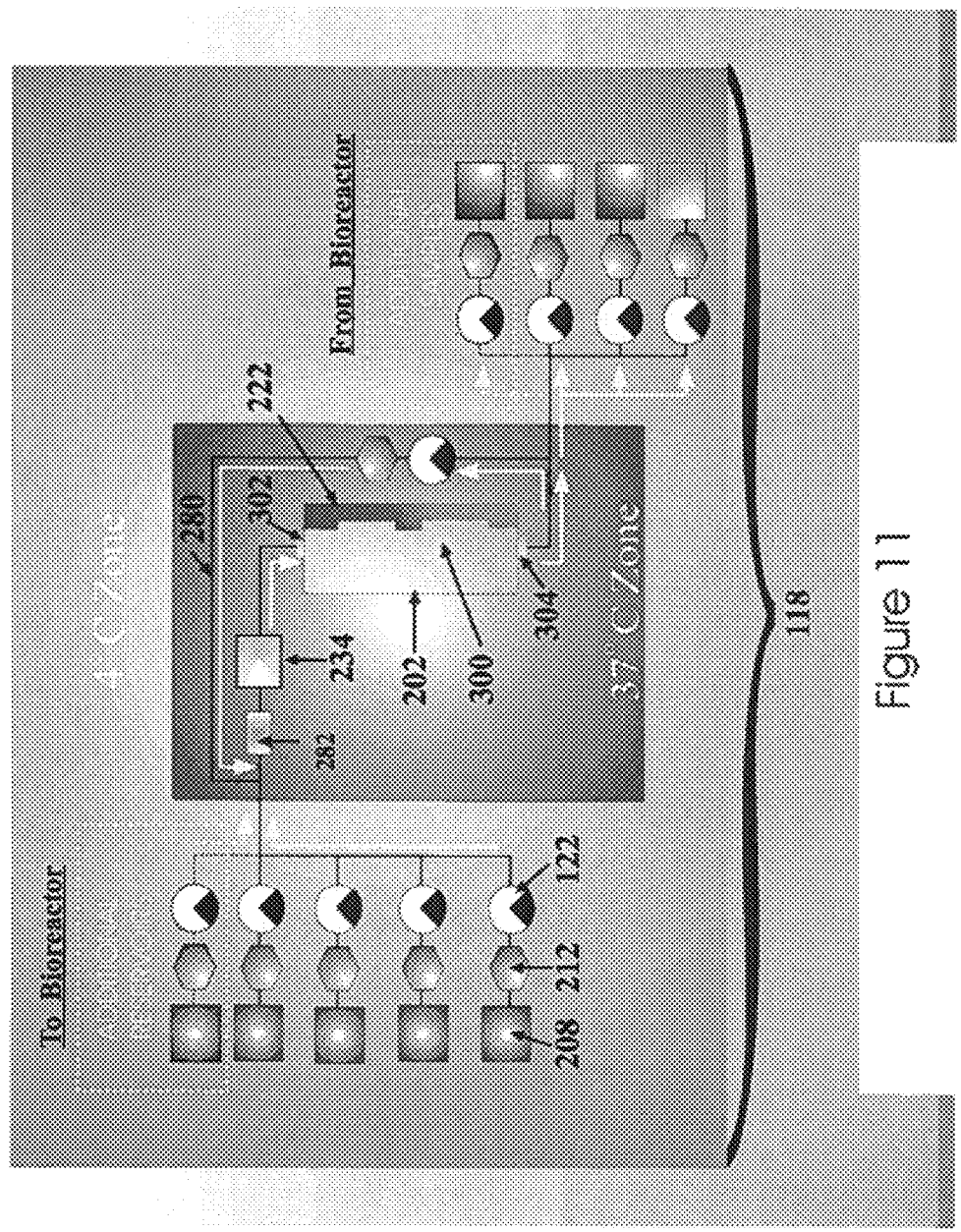
FIG. 11 shows a further embodiment of the basic tissue engineering fluid flow schematic.

FIG. 11 illustrates a variation on the basic fluid flow schematic where the fluid flow control valves are substituted for multiple pump units 122. This configuration provides enhanced operational redundancy and a reduced component count. Operation of such a system requires that any dormant pump unit prevents unregulated pass-through flow, as such an occurrence would compromise the controlled delivery of fluids.

FIGS. 12a-12d illustrate various bioreactor configurations and alternate formats for the substrates and scaffolds used for the proliferation and differentiation steps involved in the operation of the tissue engineering system. FIG. 12a shows a series of interchangeable bioreactor designs that address different bioprocessing scenarios. The Type I scenario is indicative of a basic single chamber 300 within a bioreactor 202 that accommodates a proliferation scaffold or substrate 310, or a differentiation scaffold or substrate (not shown) and is ideally suited to either proliferation or differentiation. Cells are either manually seeded onto the scaffold 310 or automatically delivered via the fluid pathway of the tissue engineering module.

The Type II scenario involves a multi-chamber bioreactor that provides for the use of a scaffold 310 (or substrate) for proliferation of the cell population and an implantable differentiation scaffold 312 that promotes the formation of a tissue construct. The culture/proliferation chamber 300 is connected to the differentiation/tissue formation chamber 306 via a funnel 314. The funnel serves to channel the cells released from the proliferation scaffold 310 into the implantable differentiation scaffold 312. The use of a filter 316 in several locations within the bioreactor serves to regulate the size of the cells or cell aggregates that can freely pass from one chamber to the next. A filter 316a is present upstream of the proliferation scaffold with the purpose of regulating the incoming cell population for the cell expansion step. Another filter 316b is present upstream of the differentiation scaffold again to control the cell population entering this step of the tissue engineering sequence. In addition, there is a further filter 316c over the outlet port 304 to prevent the loss of cells from the differentiation/tissue formation chamber during operations involving fluid transfer through the bioreactor. The filter 316 can be a filter membrane or mesh or similar type filtering material as is known to those of skill in the art.

The Type III scenario combines tissue digestion with subsequent proliferation, differentiation and tissue construct formation. In this scenario, a tissue biopsy 320 is loaded into a digestion chamber 322 present within the bioreactor 202. Digestion of the tissue biopsy occurs through the delivery of digestion enzymes into the bioreactor from one of the fluid reservoirs 208 present on the tissue engineering module. Disassociated cells exit the digestion chamber 322 under the influence of gravity sedimentation and/or fluid flow through the culture/proliferation chamber 300, and subsequently collect on the proliferation scaffold 310. Transfer of tissue aggregates out of the digestion chamber 322 is precluded by the presence of a filter membrane/mesh 316a in the flow path between the digestion chamber 322 and the culture/proliferation chamber 300. Following proliferation, the cells are released and transferred to the implantable differentiation scaffold 312 via the cell funnel 314. Again, membrane/mesh filters are present both upstream 316b and downstream 316c of the implantable differentiation scaffold 312 to ensure that the correct cell population are seeded on the scaffold and that cells are not inadvertently lost to waste during fluid transfer operations.

In the preceding scenarios, various configurations of the proliferation substrate 310 or scaffold are possible, as illustrated for example in FIG. 12b. For example, one configuration is a porous scaffold 310a having a relatively even pore gradient. A pore gradient scaffold 310b is a porous scaffold having a pore gradient where the pore size decreases as cells travel through the scaffold. This promotes a more homogeneous distribution of cells throughout the scaffold at the conclusion of the cell seeding process. A pore gradient scaffold with reversed orientation 310c may be used. Alternatively, a fiber filter scaffold 310d, may be used which is a fibrous matrix typical of organic compounds such as collagen. It is also possible to utilize a contained suspension of micro-carriers (e.g. Cytodex™) as the proliferation substrate. Furthermore, the bioreactor may have an optical probe 324 (shown in conjunction with the porous scaffold 310a) supported by the CPU 128 to enable the inspection of the cell seeding process occurring within the proliferation scaffold and to further assess the proliferation events, particularly progress toward attaining a confluent cell layer.

As with proliferation, there are a variety of implantable differentiation scaffolds 312 that may be formed in differing configuration and of diverse materials (i.e. inorganic mineral-based scaffolds such calcium phosphate, organic biopolymer scaffolds such as collagen, etc.) and employed in the tissue engineering process. FIG. 12c illustrates a multi-zone differentiation/tissue formation chamber 306 that comprises up to three implantable differentiation scaffolds 312, all of which may simultaneously proceed toward tissue construct formation. This allows for the preparation of different sizes of implantable tissue and for the use of alternate implantable differentiation scaffolds to assess and maximize tissue yield. For example, scaffold 312a is a porous reticulate formed from a bone biomaterial such as Skelite™ for use in bone and cartilage applications where the tissue construct requires hard tissue anchoring within bone. The scaffold 312a may be further enhanced through the use of a scaffold membrane/mesh 326 that encircles the implant to create a membrane encircled scaffold 312b such that the loss of cells out of the scaffold 312a during the cell seeding process is minimized, thereby making the tissue engineering process more efficient. The membrane may preferably only partially encircle the scaffold or alternatively, more fully encircle the scaffold. While the primary purpose of the scaffold membrane/mesh 326 is to contain the cells on and within the implantable differentiation scaffold 312, careful selection of the properties of the scaffold membrane/mesh 326 as is understood by one of skill in the art either allows or limits the passage of specific molecular entities that may have a marked influence on the tissue engineering process at the cellular level.

A further embodiment is a gradient porosity and membrane encircled scaffold 312c that combines the advantages of the scaffold membrane/mesh 326 with a pore gradient. The gradient is configured to deliberately cause the cells to collect on the top surface with only minimal propagation into the scaffold. A degree of porosity in the surface is considered advantageous for tissue stability and for the supply of nutrients to the developing tissue via the scaffold surface. This approach results in the development of a bipolar tissue construct with distinct stratified zones. The top zone is essentially comprised of de novo tissue. The bottom zone is essentially free of cells or tissue and remains as an open porous scaffold. The middle interfacial zone represents the structurally stable transition between the open scaffold and the de novo tissue layer. Such a bipolar tissue construct is ideal for the repair of focal defects in articular cartilage as the top layer is tissue engineered cartilage that provides for lateral integration with the host cartilage, while the bottom layer provides for lateral and axial integration with the subchondral bone. Integration of the bottom layer with the surrounding subchondral bone may be further enhanced by the application of bone marrow to the open scaffold at the time of surgical implantation. In cartilage repair applications, it is important that the mineral-based scaffold does not extend to the articular surface, as this may compromise joint function. Accordingly, a secondary non-mineral scaffold (not shown in the figures) may be employed in the top zone of de novo cartilage to assist with the formation of tissue constructs of sufficient size to treat large cartilage lesions (i.e. up to 10 $cm^2$ in diameter and 2-3 mm in thickness). Furthermore, the secondary scaffold can be configured to generate shaped constructs that have articular surface profiles that more closely match the particular anatomical characteristics present at the site of implantation. Candidate materials for the secondary scaffold are synthetic biopolymers (e.g. PGA, PLA) or natural biopolymers (e.g. alginate, agarose, fibrin, collagen, hyaluronic acid). These secondary scaffolds may be in the form of hydrogels or three-dimensional preformed scaffolds.

Alternate techniques for the preparation of bipolar tissue constructs are possible within the tissue engineering system. The implantable differentiation scaffold 312 may be partially infiltrated with a bioresorbable polymer that limits cell seeding to certain regions of the scaffold. This creates a preferential zone of new tissue formation during the preparation of the tissue construct. Upon implantation, the polymer is resorbed thereby leaving voids in the porous scaffold that promote anchorage within the host tissue. A further configuration involves an implantable scaffold with relatively open porosity that is positioned away from the exit of the differentiation/tissue formation chamber. During cell seeding, this open space provides for the collection of cells that migrate through the open scaffold. As cells are accumulated within the differentiation/tissue formation chamber, both the open space and a portion of the scaffold become infiltrated with cells and thereby create a preferential zone of new tissue formation. The resulting tissue construct comprises a de novo tissue zone that is devoid of the scaffold, a middle transition zone or interfacial zone containing both de novo tissue and the scaffold, and a region of the porous scaffold that is open and essentially free of cells or tissue.

FIG. 12d illustrates a bioreactor monitoring scheme whereby sensors 216 (i.e. temperature, pH, dissolved gases, etc) are integrated into the lid 204 of the bioreactor 202 to provide feedback to the CPU 128 of the progress of the tissue engineering process. In addition, a CCD camera 330 may be employed to monitor the optical properties of the proliferation scaffold 310 (or substrate) for evidence of impending confluence (e.g. optical density and/or light scattering as a function of cell density) such that cell release is timed to maximize the cell yield from the proliferation step.

Figure 13:
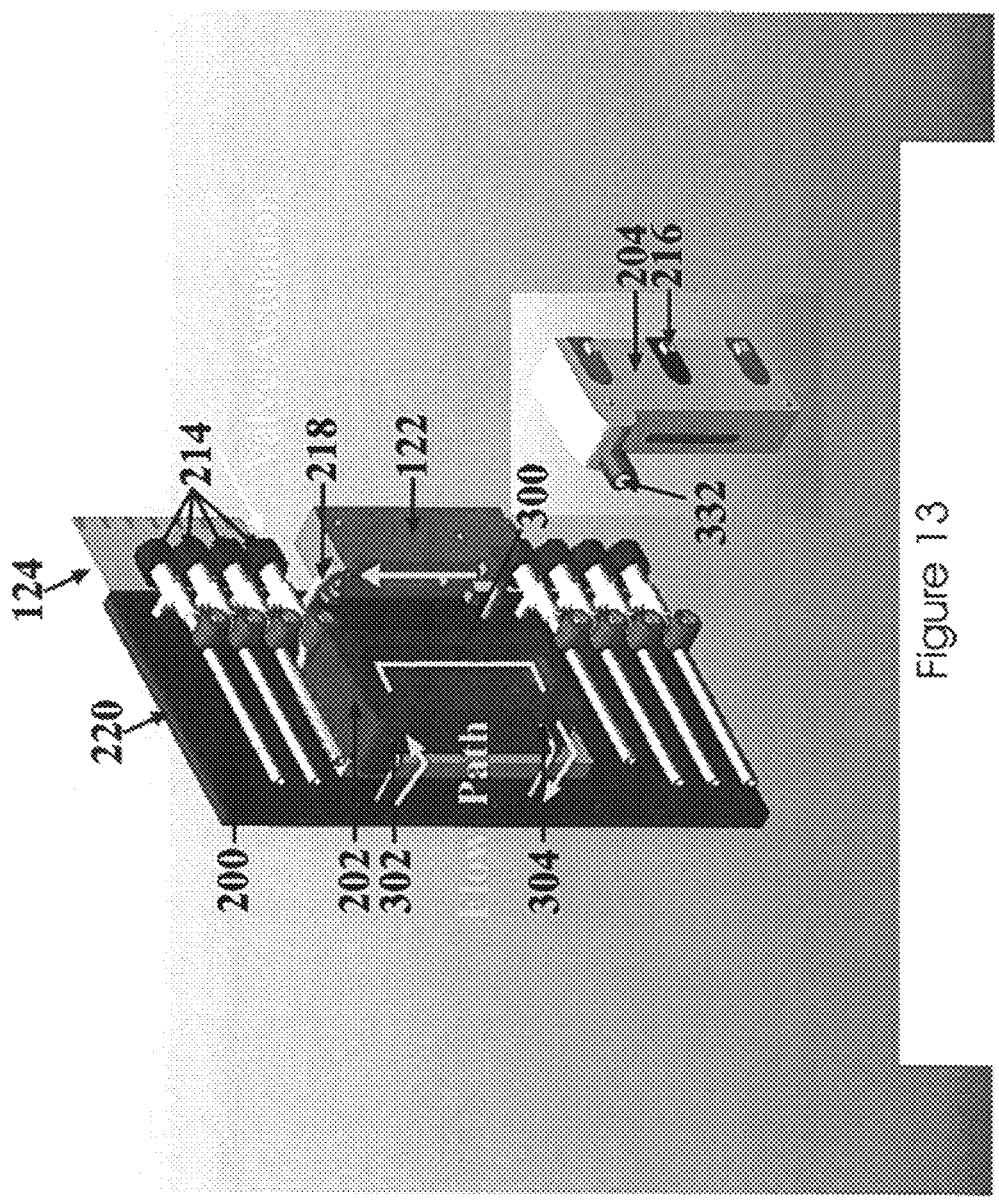
FIG. 13 shows an enlarged perspective view of the bioreactor of the tissue engineering module, illustrating the internal configuration of the bioreactor and the flow path of fluids.

FIG. 13 better shows the flow path and fluid circulation within the bioreactor 202. The bioreactor 202 is shown to have an inlet port 302, an outlet port 304 and an internal cavity defining a basic chamber 300. Fluid flows from the fluid flow plate 220 into the bioreactor 202 via the inlet port 302 and exits through the outlet port 304. The bioreactor lid 204 attaches to the bioreactor 202. A variety of different mounting hardware may be used to hold the bioreactor lid 204 and bioreactor 202 together. The chamber 300 may be designed to accommodate one or more substrates or scaffolds 310. Furthermore, the bioreactor 202 may be subdivided into separate chambers that permit the steps of tissue digestion, proliferation, differentiation, and tissue formation. Each chamber may be configured with inlet and outlet ports that are independently controlled via flow control valves for greater control over the tissue engineering sequence. Circulation of fluid is effected by the activation of one or more flow control valves 214 and the pump unit 122, based on control signals from the CPU 128. Depending upon the specific valves activated, operation of the pump unit 122 moves fluid from one of the fluid reservoirs 208 into the bioreactor 202 or permits recirculation of the fluid within the bioreactor. For biological processes that require stable dissolved gas concentrations, recirculation is advantageous as it enables the fluid to be passed across a membrane that facilitates gas exchange. The nature of the exchange is based on the dissolved concentrations in the bioreactor versus the external conditions established by the ECU 136. The bioreactor lid 204 is shown to have a sampling port 332 and sensor probes 216 that are operably connected to the interior chamber of the bioreactor. Alternatively, the sampling port may be provided elsewhere on the bioreactor housing. The sampling port allows the removal or addition of materials into and out from the bioreactor. The sampling port may be replaced or augmented with a gas exchange membrane as required.

Figure 14:
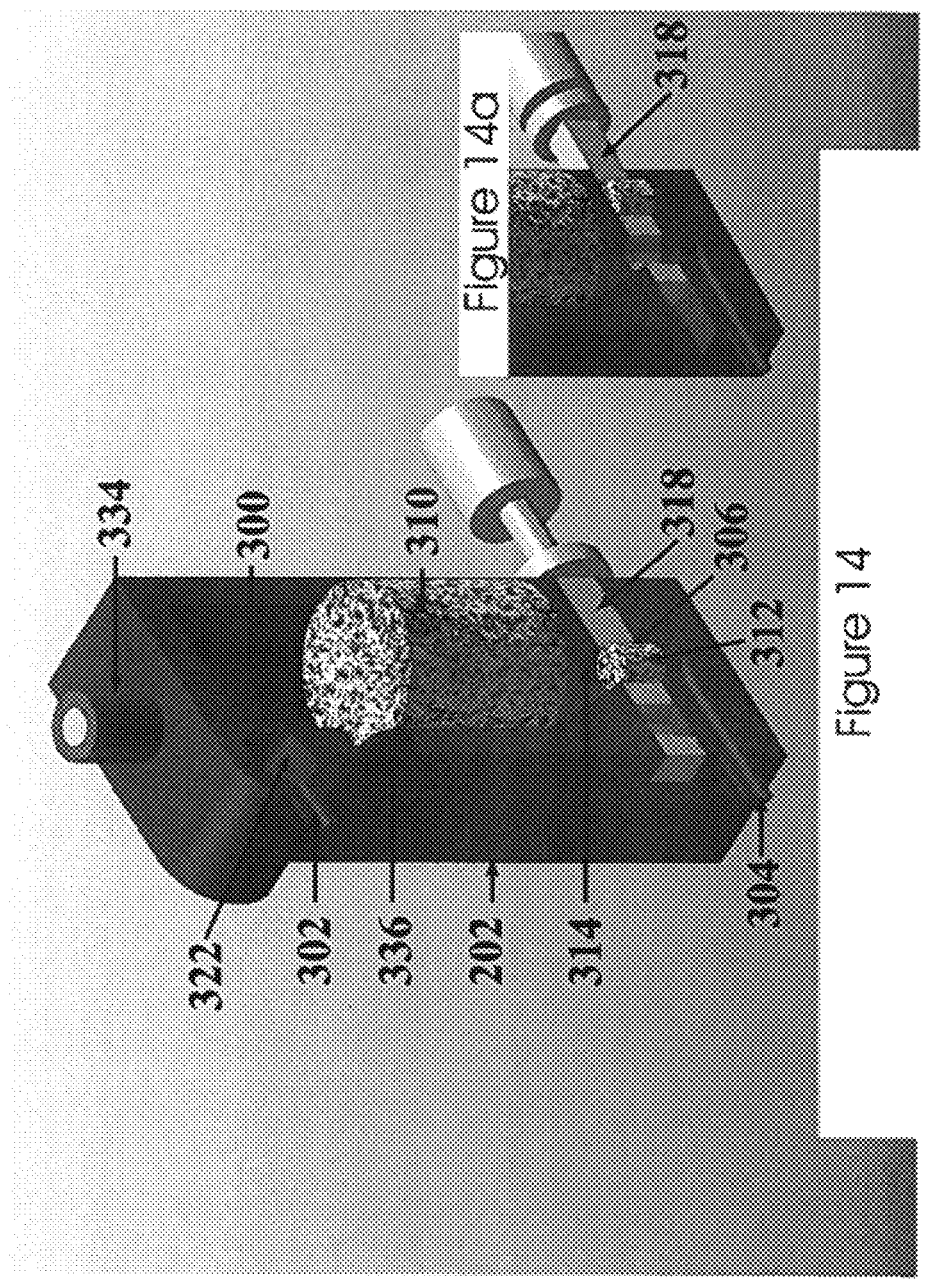
FIG. 14 shows a further embodiment of the bioreactor of the tissue engineering module, illustrating the internal configuration of the bioreactor.

FIG. 14 illustrates a multi chamber bioreactor 202 with the bioreactor lid 204 removed for clarity. The inlet port 302 is connected to a tissue digestion chamber 322. The configuration of the tissue digestion chamber 322 permits a patient biopsy to be loaded into the bioreactor for subsequent automated digestion to yield disassociated cells. The circulation path within the digestion chamber promotes the gentle agitation of the biopsy to prevent stagnant areas that could potentially lead to excessive exposure of the biopsy tissue to circulating digestion enzymes. Furthermore, the inlet and/or outlet of the digestion chamber may house a filter membrane/mesh 316 (not shown) of varying porosity to provide for cell sorting and to preclude the release of partially digested tissue aggregates. The bioreactor contains a second chamber 300 that accommodates a proliferation substrate or scaffold 310 for receiving cells for proliferation. The proliferation scaffold may be formed in various geometries that support both two-dimensional and three-dimensional proliferation, and may be comprised of various biocompatible materials that promote cell proliferation, such as calcium phosphate biomaterials (for example Skelite™), biopolymers, or natural matrices (for example collagen). Cells delivered from the tissue digestion chamber 322, or via the optional cell inoculation port 334, become dispersed on or within the proliferation substrate or scaffold 310 and proliferate, thereby increasing the cell population for subsequent cell differentiation and tissue formation. Note that the process may be terminated following proliferation if the goal is to only expand the cell population without further differentiation. An implantable differentiation scaffold 312 is present within a differentiation/tissue formation chamber 306 at the base of the bioreactor 202. As with the proliferation scaffold 310, the implantable differentiation scaffold 312 may be formed in different geometries and may be composed of a variety of biocompatible materials that are properly selected to meet the biological requirements of the implant site, (for example Skelite™ is an ideal candidate implant for skeletal sites).

In operation, cells are released from the proliferation substrate or scaffold 310 through an automated sequence, such as the delivery of enzymes (for example trypsin) and the timed application of impact to the bioreactor via the impact drive 266 (not shown). The cell suspension migrates under the controlled flow conditions present in The bioreactor into the implantable scaffold 312 via the cell funnel 314, whereupon the cells become resident and initiate the differentiation and tissue formation sequence. Upon conclusion of this sequence, the tissue so formed may be removed from the bioreactor for subsequent implantation. One skilled in the art would understand that the particular embodiment of the bioreactor of FIG. 14 is only a representative design example. The bioreactor, in general, can be configured in various ways with respect to overall shape, size and internal configuration without adverse effect on function. For example, a gas exchange membrane 336 present on the bioreactor may be a separate and discrete component that is connected in-line with one or more fluid delivery tubes 210 or the flow plate 220 of the tissue engineering module 118. Furthermore, the chambers of the bioreactor may be isolated from each other via control valves to avoid the necessity for all fluids to pass through all chambers. When required the passageways between chambers may be opened to effect the transfer of fluids and cell suspensions. An example of such a variation that enables increased flexibility in bioprocessing conditions and sequences is illustrated in FIG. 17. An alternate configuration to enable controlled exposure of the implantable differentiation scaffold 312 to the contents of the bioreactor is the use of a shuttle 318 that isolates the implantable scaffold until cell seeding is required as part of the differentiation step. To enable cell seeding, the shuttle 318 moves the Implantable scaffold into the fluid flow from a protected location within the bioreactor. Various configurations of the shuttle are possible, including rotation-based movement or the use of a removable barrier that isolates the implantable scaffold until cell seeding is required.

Figure 15:
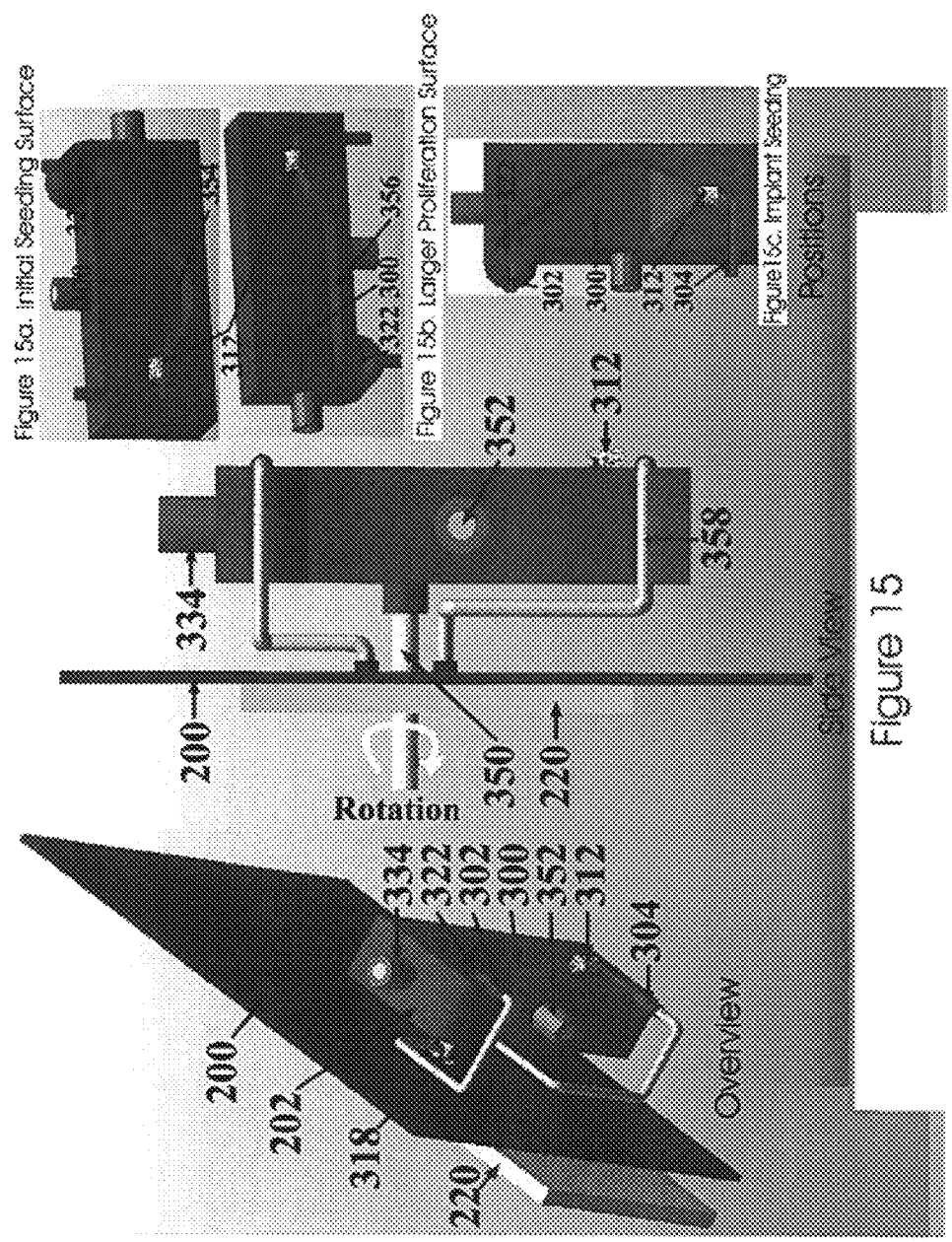
FIG. 15 shows a rotatable bioreactor design.

FIG. 15 illustrates a rotational bioreactor design that takes advantage of the orientation of the gravity vector to effect cell transport by sedimentation at different stages in the tissue engineering process. Note that while this figure illustrates rotation of the bioreactor, the technical objective may be equally attained by rotation of the tissue engineering module or indeed by rotation of the entire housing 102. As shown in FIG. 15, the bioreactor 202 is attached to a rotational shaft 350 which is affixed to the structural spine 200 of the tissue engineering module 118. This provides a mechanism for the rotation of the bioreactor 202 in order that cell seeding via sedimentation can occur on to selected proliferation surfaces within the culture/proliferation chamber 300. The proliferation surfaces of the bioreactor may be optionally coated with biomaterials that enhance proliferation (for example Skelite™), or a dedicated proliferation substrate or scaffold may be inserted into the chamber 300 to provide this role. As an alternative to the use of the digestion chamber 322, a second inoculation port 352 is provided at the side of the bioreactor 202 to enable direct cell seeding. Cells may be initially seeded on a proliferation surface 354 which is relatively small (FIG. 15a). Based on elapsed proliferation time or the detection of confluence, the cells may be automatically released and the bioreactor rotated via the rotational shaft 350 such that the cells released from the proliferation surface 354 will sediment on to the increased area of surface 356 (FIG. 15b), allowing further proliferation. At the completion of the secondary proliferation step, the expanded cells are released and the bioreactor is again rotated to permit seeding of the implantable scaffold 312 (FIG. 15c). Thus the rotational shaft 350 and associated flexible tubes 358 allow the bioreactor 202 to be rotated as required to maximize the use of gravity sedimentation in sequential proliferation stages. It is within the scope of the present invention to use the rotational shaft in a manner to agitate or shake the bioreactor where such conditions are desirable.

Figure 16:
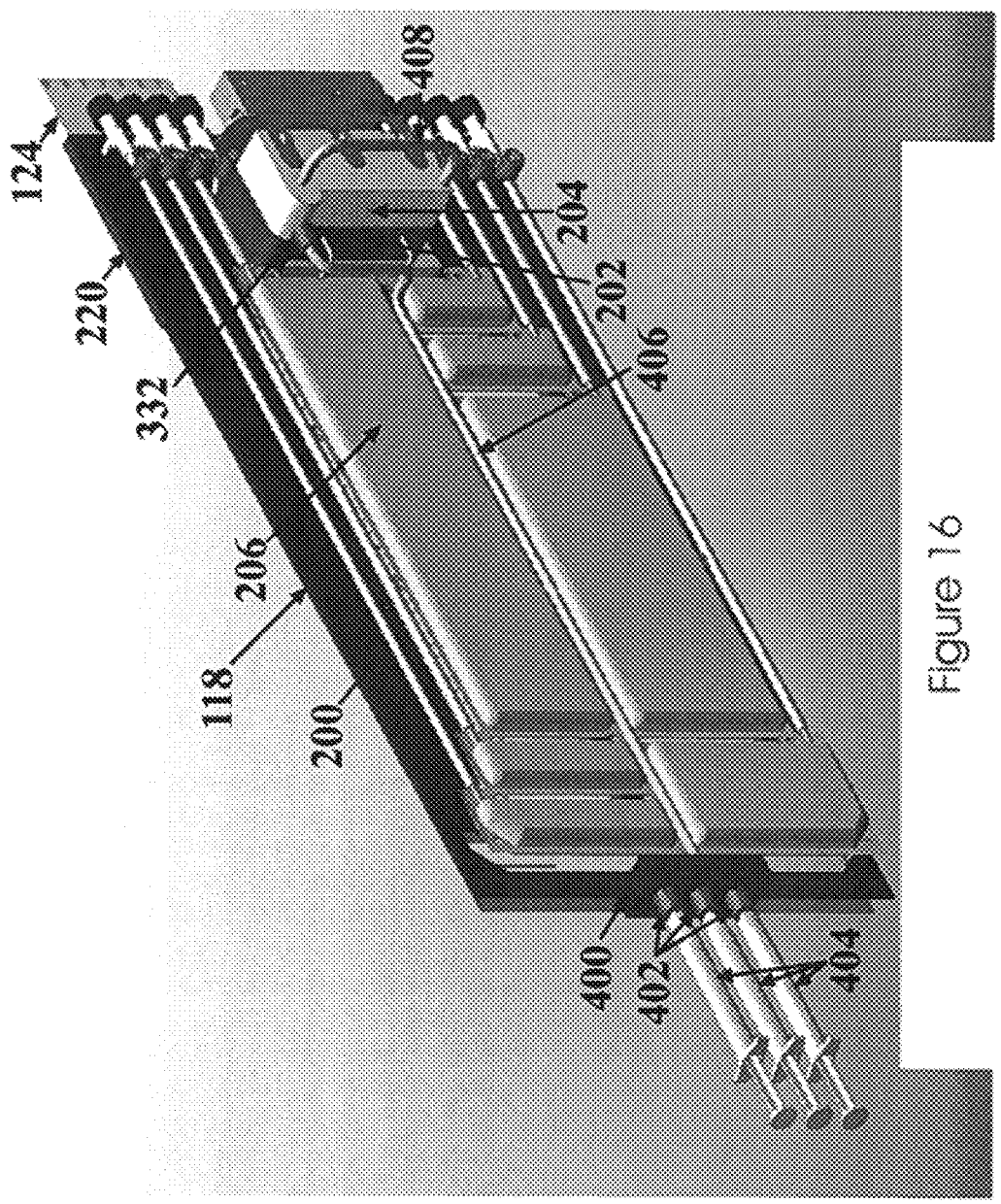
FIG. 16 shows the sterile sampling embodiment of the tissue engineering module.

Referring now to FIG. 16, the tissue engineering module 118 may be adapted to include techniques for the sterile sampling of suspended cells, tissue culture fluids, and/or waste products. In this embodiment, a syringe manifold 400 and sterile offloading ports 402 are integrated into the structural spine 200 of the tissue engineering module 118. Microbore tubing 406 links the syringe manifold to the bioreactor 202 via the sampling port 332. Syringes 404 are connected to offloading ports 402 at the manifold 400 to enable the collection and removal of fluid samples or cell suspensions for subsequent analysis without compromising the operation, integrity or sterility of the tissue engineering process. An alternate sampling technique is also provided whereby a fusible bioreactor sampling line 408 is connected to the bioreactor lid 204. As this line is physically linked to the interior of the bioreactor and is in close proximity to the biological events underway therein, the line contains fluid of substantially the same composition as that present within the bioreactor. Consequently, a representative sample of the bioreactor fluid may be obtained by fusing the ends of the sampling line and then removing the line from the tissue engineering module for subsequent analysis. It will be obvious to one skilled in the art that such a fusible line can be used as the basis for a sampling technique through the automatic operation of sealing components within the housing 102.

FIG. 17 illustrates a more complex fluid flow schematic for the tissue engineering module 118 in which the different requirements for digestion, proliferation and differentiation are accommodated by separate bioreactor chambers. These chambers may be present within a series of discrete bioreactors or combined within a single bioreactor that maintains separate control over the conditions in each chamber. A tissue digestion chamber 322 is present that accommodates a tissue biopsy 320. A proliferation chamber 300 is present that is configured to accept cells from the digestion chamber 322 and allows seeding of a proliferation substrate or scaffold 310. A differentiation/tissue formation chamber 306 is also present that is configured to accept the expanded cell numbers from the proliferation chamber 300 and allows seeding of an implantable scaffold 312.

Tissue engineering reagents (I.e. media, enzyme solutions, washing solutions, etc.) are loaded in fluid reservoirs 208a-208e. Waste products are collected in fluid reservoir 208f, which can be manually aspirated for sampling purposes using access port 212f. Additional fluid reservoirs may form part of the fluid reservoir system 206 and be accommodated on the tissue engineering module as required for different tissue engineering processes. Fluid flow through the system is directed by the operation of fluid pumps 122a-122k, flow control valves 214a-214c, and uni-directional flow valves 410a-410c (i.e. fluid flow check valves). Furthermore, pumps 212a-212k are configured to operate as active pumps or passive valves (open/closed), according to control inputs from a central microprocessor. Filters 316a-316d are used to selectively control the movement of cell suspensions within the system and to limit the passage of cell aggregates during washing and transition stages of the tissue engineering process. Levels of dissolved gasses in the media are maintained via the in-line gas exchange membranes 282a and 282b. Optional syringes 404a and 404b are present to allow cell collection or media sampling via sterile offloading ports 402a and 402b.

In operation, a tissue biopsy 320 is inserted into the tissue digestion chamber 322 between filters 316a and 316b. A digestion medium containing enzymes is pumped into the tissue digestion chamber 322 from the fluid reservoir system 206 to initiate the digestion process. Digestion may be enhanced by gentle agitation of the digestion medium within the digestion chamber via a mixing diaphragm to maximize reagent exposure to the biopsy. The digestion medium may be continuously or periodically re-circulated via pump 122g. During recirculation, the fluid flow is directed into the bottom of the digest chamber, against the gravity vector, in order to suspend and tumble the tissue biopsy, thereby maximizing the effectiveness of the digestion process. Filter 316a prevents migration of cells and cell aggregates into the fluid pathway. The recirculation path includes the in-line gas exchange membrane 282a which provides for consistent levels of dissolved gases in the digestion medium. Introduction of a washing solution, contained in the fluid reservoir system 206, into the bottom of the digestion chamber 322 flushes the digestion chamber and effectively washes the digestion medium from both the disassociated cells and any residual cell aggregates. Following a single or multiple washing procedures, the application of reverse flow transfers the cell suspension to either the proliferation chamber 300 or the optional syringe 404a for external inspection or analysis. The transfer of partially digested tissue out of the digestion chamber is precluded by filter 316b that is sized to allow passage of disassociated cells and retention of cell aggregates.

Cells generated from the biopsy digestion process or available via direct loading of a cell suspension are seeded through fluid flow and/or gravity sedimentation onto a proliferation substrate or scaffold 310 present within the proliferation chamber 300. Following a quiescent period to allow attachment of the cells to the proliferation substrate or scaffold 310 (for the example of attachment dependent cells), a proliferation medium is introduced into the proliferation chamber 300 from the fluid reservoir system 206. This medium is periodically replaced with fresh proliferation medium from the reservoir system 206 at specific times during the proliferation phase. In between the medium replacement steps, the fluid within the proliferation chamber is continuously or periodically recirculated under the control of pumps 122g, 122h and 122i, plus control valves 214a and 214b. The fluid delivery and recirculation paths include the in-line gas exchange membrane 282a which provides for consistent levels of dissolved gases in the proliferation medium. During a medium replacement step, the supply of fresh medium from the fluid reservoir system 206 is balanced by the removal of fluid to the waste reservoir 208f via pump 122f. Thus, through a combination of periodic medium replacement steps and controlled recirculation, the tissue engineering system maintains optimal conditions within the proliferation chamber throughout the proliferation process.

Once the cell culture approaches confluence, the media within the proliferation chamber 300 is evacuated into the waste reservoir 208f by pump 122f. In this process, the removal of fluid from the proliferation chamber is balanced by incoming sterile air delivered via a sterile filter port on the proliferation chamber (not shown) or by incoming PBS wash solution from the fluid reservoir system 206. The cells are washed extensively by two consecutive washing steps with the PBS wash solution to remove residual proliferation medium. The cells are subsequently released from the proliferation substrate or scaffold 310 through an automated sequence, such as the delivery of enzymes (for example trypsin) and the timed application of impact to the bioreactor via an impact drive. Following cell release, the enzymatic process may be stopped by the delivery of media containing serum that inhibits enzyme activity. In order to collect the cells for eventual seeding on to the implantable scaffold 312 within the differentiation/tissue formation chamber 306, the cell suspension is transferred from the proliferation chamber 300 to the filter 316c. The filter 316c prevents the passage of cells but allows the media to continue via valve 214b to the waste reservoir 208f under the control of pump 122f. The collected cells are then released from the filter 316c by the application of reverse flow and are delivered to either the differentiation/tissue formation chamber 306 or the optional syringe 404b for external inspection or analysis.

Cell seeding on to the implantable differentiation scaffold 312 is achieved by transferring the cells from the filter 316c to the top surface of the scaffold via pump 122j. The loss of cells away from the scaffold is minimized by the optional use of a scaffold membrane or mesh 326. Following cell seeding, fresh differentiation media may be introduced into the differentiation/tissue formation chamber 306 through a secondary input by the operation of pump 122k. This secondary input is located away from that region of the implantable scaffold that is seeded with cells so as to minimize the potential for damaging sheer stresses that could compromise the formation of cell aggregates. The differentiation medium is periodically replaced with fresh differentiation medium from the reservoir system 206 at specific times during the differentiation phase. In between the medium replacement steps, the fluid within the differentiation/tissue formation chamber is continuously or periodically recirculated under the control of pumps 122j or 122k, plus control valve 214b. The path for the delivery of both fresh differentiation medium and recirculated medium includes the in-line gas exchange membrane 282b which provides for consistent levels of dissolved gases in the differentiation medium. During a medium replacement step, the supply of fresh medium from the fluid reservoir system 206 is balanced by the removal of fluid to the waste reservoir 208f via pump 122f. Environmental conditions within the differentiation/tissue formation chamber are monitored and controlled for the period necessary for the successful formation of the tissue construct, at which time the differentiation/tissue formation chamber of the bioreactor is opened and the construct retrieved for subsequent clinical or research use.

Figure 18:
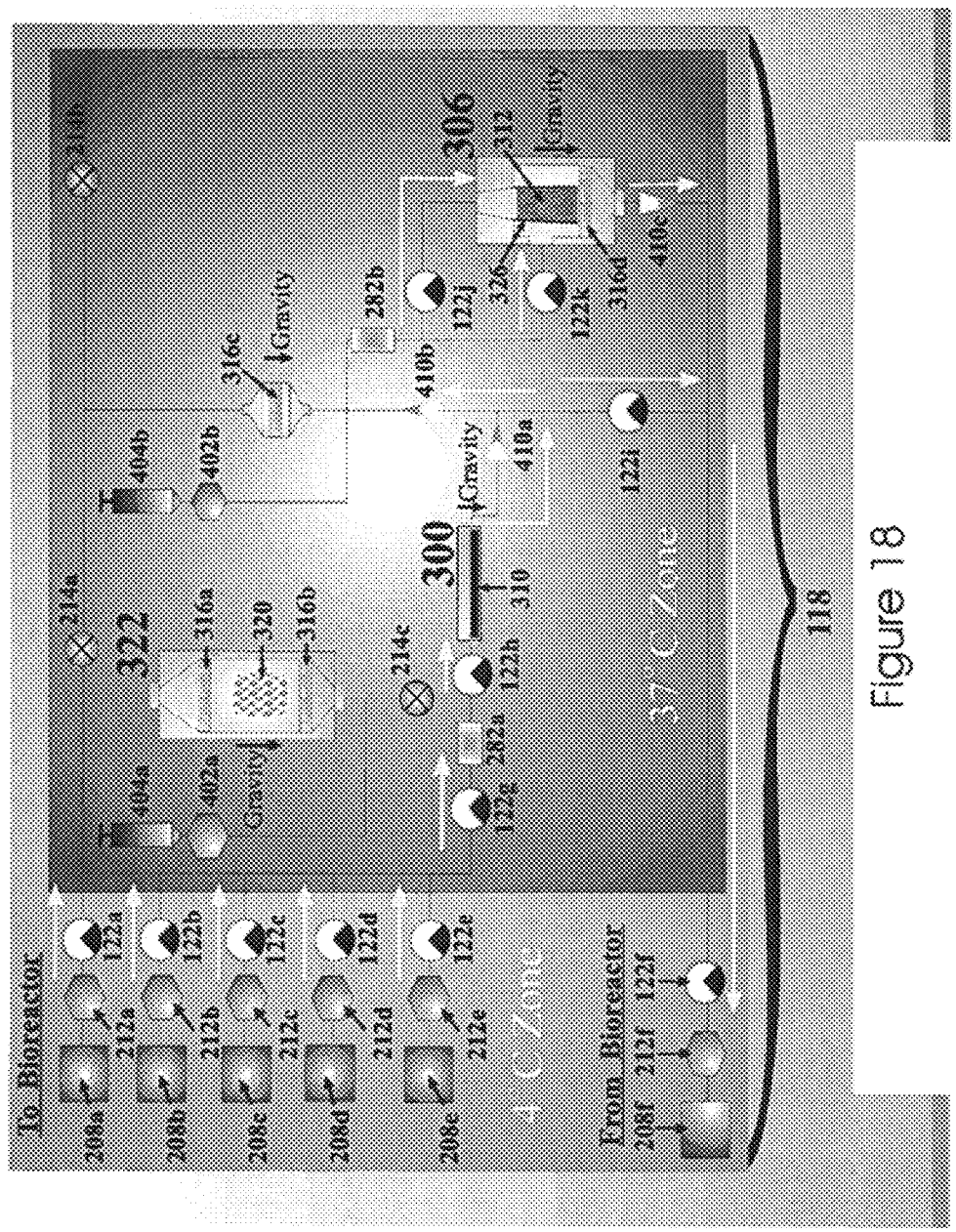
FIG. 18 shows yet a further embodiment of the tissue engineering fluid flow schematic.

FIG. 18 illustrates a variation on the fluid flow schematic of FIG. 17 where the proliferation scaffold or substrate 310 within the proliferation chamber 300 is replaced with a planar proliferation substrate of relatively large surface area. The orientation of the substrate is such that cell sedimentation under gravity evenly distributes the cells over the proliferation surface. Provided that the correct orientation of the proliferation chamber is maintained, the proliferation substrate may be in the form of a rigid polymer culture plate or a flexible wall container.

Figure 19:
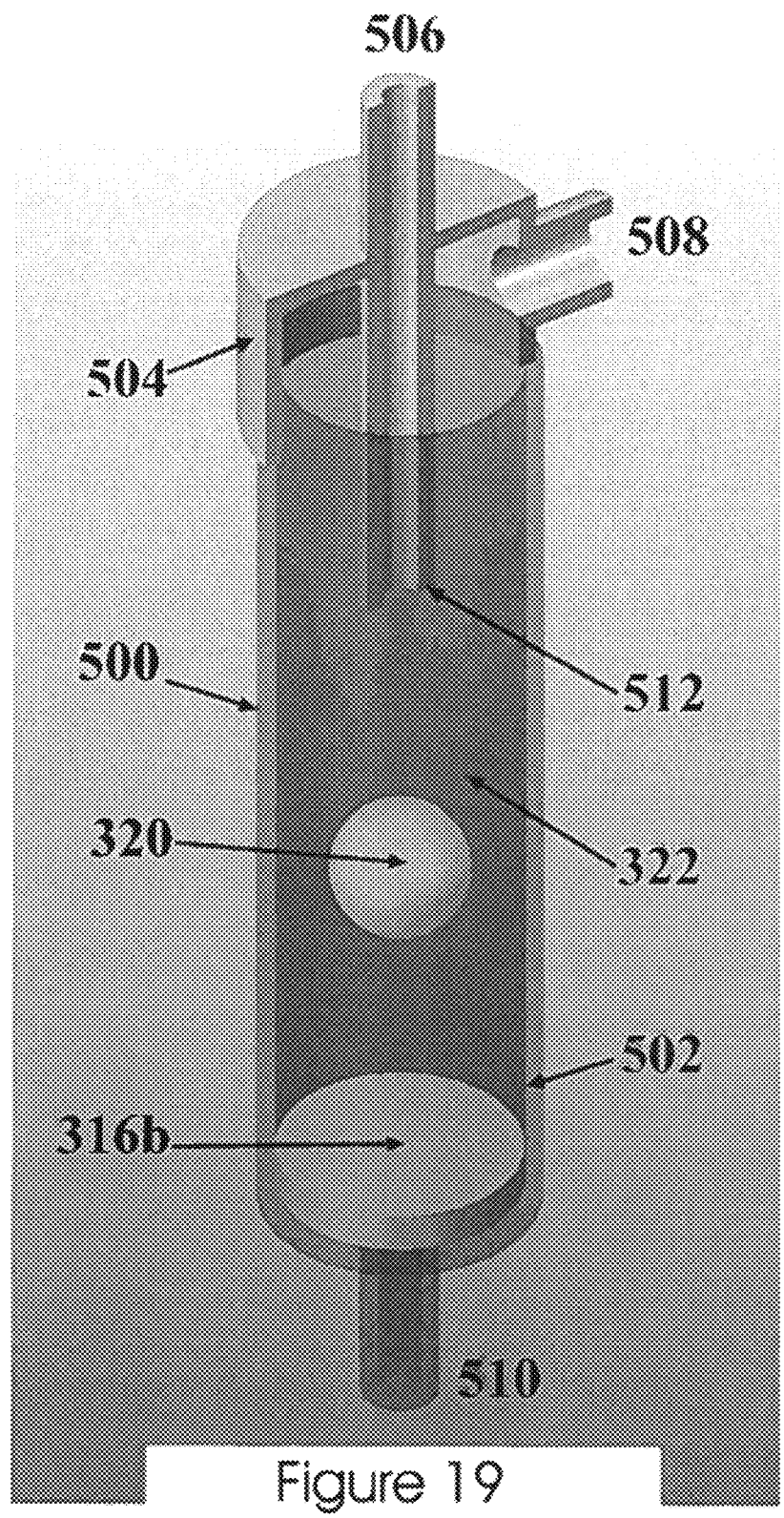
FIG. 19 shows a bioreactor design suitable for tissue digestion and cell collection.

FIG. 19 shows a tissue digestion bioreactor 500 that contains a tissue digestion chamber 322 of an appropriate size to accommodate one or more tissue samples such as a tissue biopsy 320. The bioreactor 500 consists of four primary components: a bioreactor base 502 that substantially forms the tissue digestion chamber 322, a removable bioreactor lid 504, port filter 316b, and optional port filter 316a (not shown).

The bioreactor lid 504 provides for a media port 506 with an optional port filter 316a (not shown) and an air outlet port 508. The bioreactor base 500 accommodates filter 316b that allows passage of disassociated cells out of the tissue digestion chamber 322, via media port 510, and retention of tissue aggregates and biopsy debris.

Following insertion of the tissue biopsy 320, the bioreactor is filled under automated control with an enzyme solution through port 506 or port 510. The addition of enzyme solution to the tissue digestion chamber 322 is balanced by air escaping through port 508. Biopsy digestion takes place under continuous or intermittent recirculation of the enzyme solution, thereby keeping the released cells in suspension and maximizing the exposure of the biopsy to the enzyme reagents. During recirculation, the enzyme solution enters the bioreactor through port 510 and leaves via port 506. This creates a fluid flow path in a direction opposite to the gravity vector such that the biopsy is suspended and tumbled to maximize the effectiveness of the enzyme reagents. Digestion may be enhanced by gentle agitation of the digestion medium within the digestion chamber via a mixing diaphragm (not shown). Port 508 may be closed during any recirculation steps, as air bubbles present in the fluid flow system are trapped in the upper half of the bioreactor, above the inlet 512 of port 506. Upon completion of the digestion sequence, the application of reverse flow of either air or medium through port 506 transfers the disassociated cells through port 510 to either a proliferation chamber or a cell collection vessel.

Figure 20:
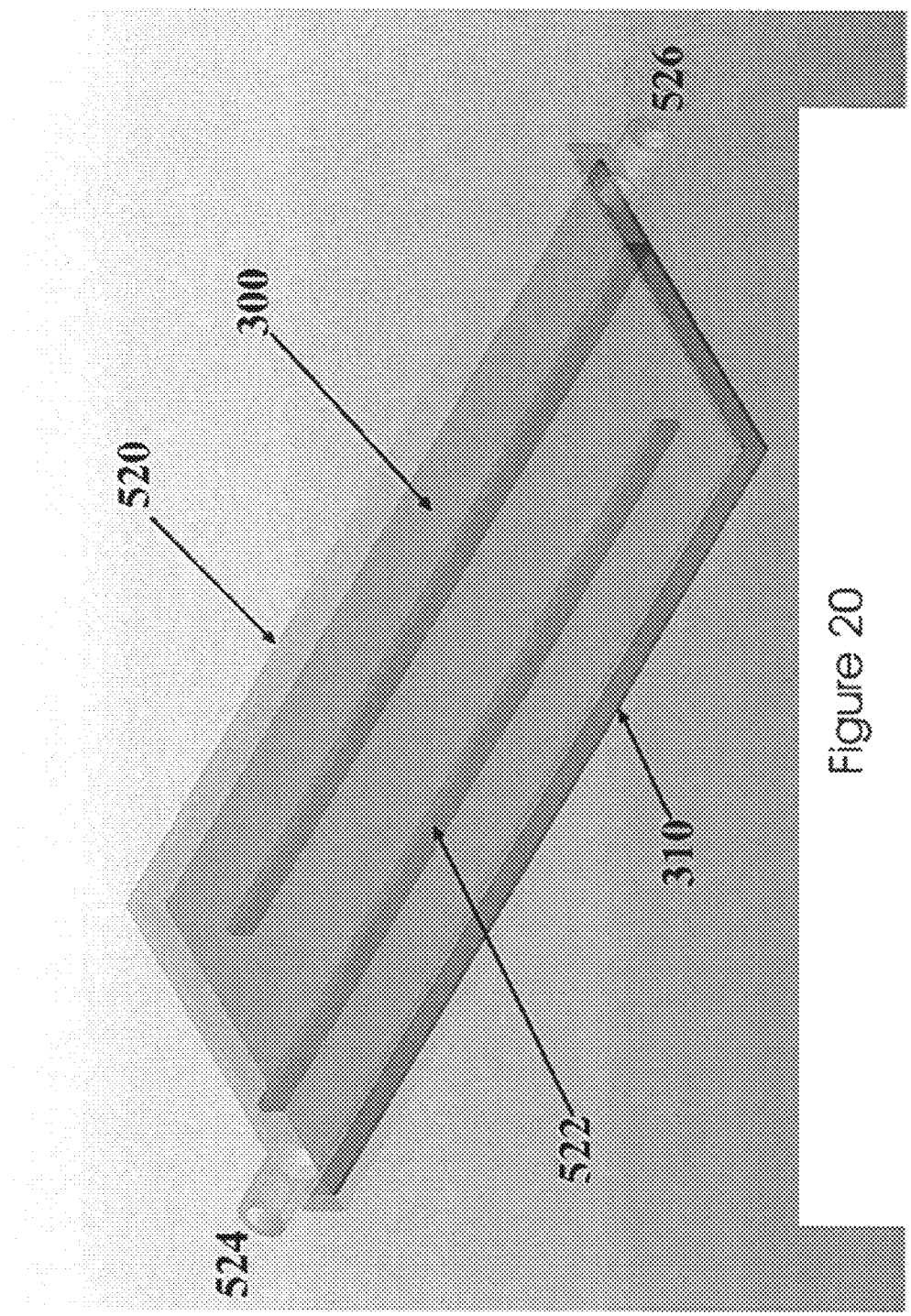
FIG. 20 shows a bioreactor design suitable for cell proliferation.

FIG. 20 shows a proliferation bioreactor 520 that provides for a proliferation chamber 300. The bottom of the proliferation chamber consists of proliferation substrate 310 suitable for cell attachment and growth. To adjust or maintain the levels of dissolved gases in the medium, a gas permeable membrane (not shown) may be incorporated to the top surface of the proliferation chamber that allows the transport of gases such as oxygen and $CO_2$. Separation walls 522 divide the internal space of the proliferation chamber into a channel system that forces medium to follow a predefined pathway from the inlet port 524 to the outlet port 526.

The design of the proliferation bioreactor design has several important operational features. Relatively uniform cell seeding can be obtained by the infusion of a cell suspension through the channel system. Furthermore, the channel configuration ensures that media flow is well distributed over the whole proliferation surface, thereby reducing potential low-flow regions that may compromise local cell vitality due to reduced nutritional supply or waste product removal. At the conclusion of the proliferation sequence, continuous or intermittent recirculation of an appropriate enzyme solution through the channel system induces uniform cell detachment due to the effect of the enzyme reaction and the low-level sheer stresses generated by the fluid flow. Accordingly, cell harvest is achieved without the need for mechanical shaking or rotation of the proliferation chamber.

Figure 21:
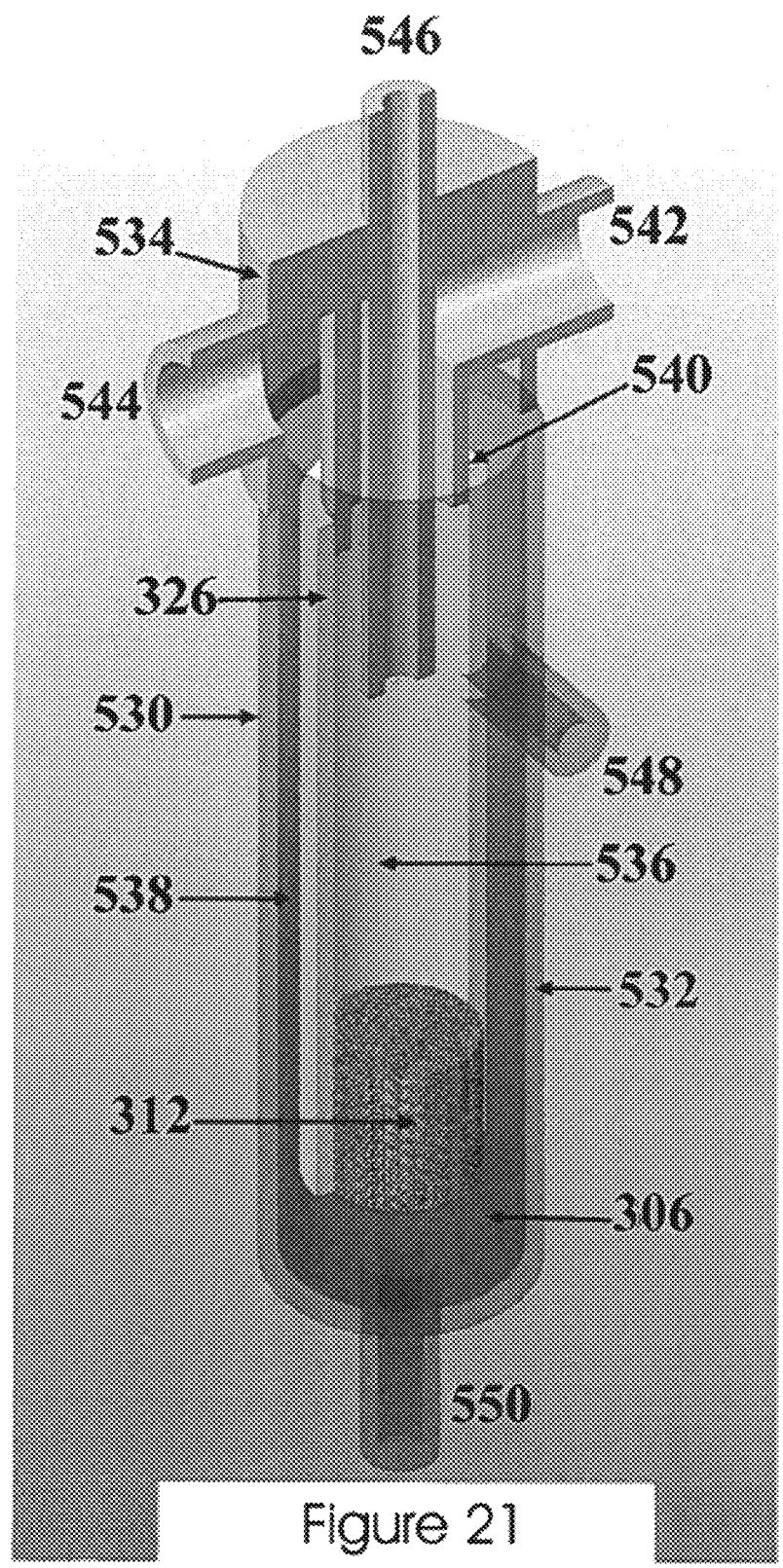
FIG. 21 shows a bioreactor design suitable for cell differentiation and tissue construct formation.

FIG. 21 shows a differentiation bioreactor 530 designed to promote cell differentiation and subsequent tissue construct formation. The bioreactor consists of four primary components: a bioreactor base 532 that substantially forms a differentiation/tissue formation chamber 306, a removable bioreactor lid 534, a permeable membrane tube 326, and a differentiation scaffold 312. The permeable membrane tube 326 tightly encircles the scaffold reticulate to form a tissue growth compartment 536 above the scaffold. The tissue growth compartment may extend within the scaffold according to the pore size of the scaffold and the placement of the scaffold within the membrane tube. The membrane tube is also affixed to the inlet 540 of port 542, such that the membrane is physically located centrally within the differentiation/tissue formation chamber 306. This divides the bioreactor into two independent compartments, a cell and tissue growth compartment 536 and an outer cell-free medium compartment 538, all within the overall differentiation/tissue formation chamber 306. The pore size of the membrane tube is selected on the basis of being impermeable for cells but permeable for nutrients, waste products, growth factors, etc., within the culture medium. If desired, membrane pore size can be chosen in a manner to exclude molecules of a certain molecular weight from passing through the membrane.

The bioreactor lid 534 has two air outlets ports 542 and 544, and one media inlet port 546. The bioreactor base 532 accommodates two further ports 548 and 550. The inlet port 546 is required for loading a cell suspension into the tissue growth compartment 536 and for the perfusion of the emerging tissue construct with culture medium. During the delivery of the cell suspension into the empty tissue growth compartment, entrapped air is allowed to exit through port 542. In a similar fashion, the outer cell free compartment 538 is loaded with media via port 548 or port 550 and entrapped air may escape via port 544.

The design of the differentiation bioreactor allows direct perfusion of the tissue construct through media delivery to port 546 or indirect media supply to the surrounding cell free compartment 538 via port 548. Typically, ports 542 and 544 are closed during perfusion and port 550 serves as a media outlet; however, various alternate media supply scenarios are possible based on specific tissue engineering requirements. An important aspect of the media perfusion strategy is that the permeable membrane 326, which forms part of the tissue growth compartment, allows fresh culture medium to permeate into the tissue growth compartment without any loss of cells away from the scaffold. Furthermore, nutrition is provided to the cells from essentially all directions without restrictions from any impermeable bioreactor walls.

Figure 22:
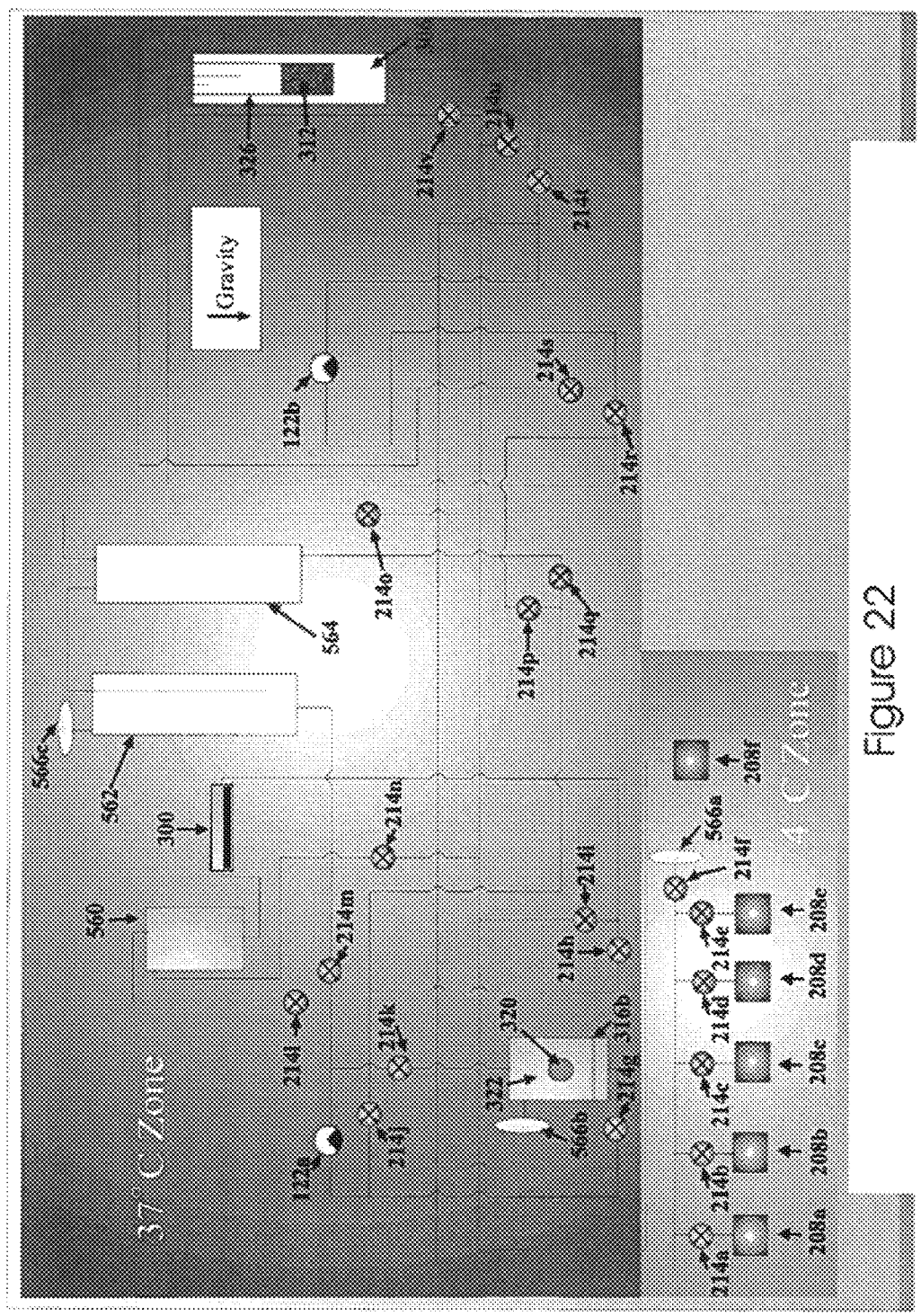
FIG. 22 shows yet a further embodiment of the tissue engineering fluid flow schematic.

FIG. 22 illustrates a further embodiment of the fluid flow schematic in which the bioreactors of FIGS. 19-21 may be employed. A tissue digestion chamber 322 is present that accommodates a tissue biopsy. A proliferation chamber 300 is present that is configured to accept cells from the digestion chamber 322 and allows seeding of a proliferation substrate. A bubble trap 560 removes air bubbles from the input line to the proliferation chamber and therefore prevents these bubbles from entering the proliferation chamber 300 and potentially compromising localized cell populations. A reservoir 562 is present to accept the expanded cell numbers from the proliferation chamber 300 and to serve as a temporary holding container during a cell washing and cell concentration procedure performed with the aid of a cross flow filtration module 564. A differentiation/tissue formation chamber 306 is also present that is configured to accept the cells from reservoir 562 after the washing and concentration step and allows seeding of an implantable scaffold 312.

Tissue engineering reagents (i.e. media, enzyme solutions, washing solutions, etc.) are stored in fluid reservoirs 208a-208e. Waste products are collected in fluid reservoir 208f. Fluid flow through the system is directed by the operation of fluid pumps 122a and 122b, flow control valves 214a-214v according to control inputs from a central microprocessor. Air filters 566a-566c allow the transfer of air into or out of the system as required during operation without compromising system sterility. Furthermore, in-line gas exchange membranes (not shown) may be deployed at various locations within the fluid flow paths to facilitate the control of dissolved gases in the culture medium.

In operation, a tissue biopsy 320 is inserted into the tissue digestion chamber 322. A digestion medium containing enzymes is pumped into the tissue digestion chamber 322 from a fluid reservoir 208 to initiate the digestion process. The digestion medium may be continuously or periodically re-circulated via pump 122a, thereby keeping the released cells in suspension and maximizing reagent exposure to the biopsy. Introduction of a proliferation culture medium from one of the fluid reservoirs 208 into the top of the digestion chamber 322 transfers the cell suspension to the proliferation chamber 300 and simultaneously dilutes the enzyme solution to a concentration that is tolerable for cell proliferation in the in the proliferation chamber 300. The transfer of partially digested tissue out of the digestion chamber is precluded by port filter 316b that is sized to allow passage of disassociated cells and retention of cell aggregates. Cells generated from the biopsy digestion process are homogeneously distributed throughout the proliferation chamber 300 either by the recirculation of the cell suspension via the activation of valves 214h, 214J, 214I and the pump 122a, or by the automated application of gentle shaking of the proliferation bioreactor.

Following a quiescent period to allow attachment of the cells to the proliferation substrate, the proliferation medium is periodically or continuously replaced with fresh proliferation medium from one of the fluid reservoirs 208. During a medium replacement step, the supply of fresh medium from the fluid reservoir system 208 is balanced by the removal of fluid to the waste reservoir 208f via valve 214i.

Once the cell culture approaches confluence, the media within the proliferation chamber 300 is evacuated into the waste reservoir 208f. In this process, the removal of fluid from the proliferation chamber is balanced by incoming sterile air delivered via a sterile filter 566a or by incoming PBS wash solution from one of the fluid reservoirs 208.

The cells are subsequently released from the proliferation substrate through an automated sequence, such as the delivery of enzymes (for example trypsin) and the timed recirculation of the cell suspension or the timed application of impact or agitation to the bioreactor via an impact drive. In order to remove the enzymes and to collect the cells in a relatively small volume of medium for subsequent transfer to the cell differentiation chamber 306, the cell suspension is transferred from the proliferation chamber 300 to the reservoir 562. The cell suspension is then continuously recirculated via valves 214m, 214j, 214q and pump 122a through the cross-flow filtration module 564. The membrane in the cross flow filtration module 564 prevents the loss of cells but allows a certain percentage of media (permeate) to be removed via valve 214o to the waste reservoir 208f. The consequence is a reduction of the suspension volume and/or dilution of any enzymes present, provided the removal of permeate is compensated by the supply of fresh medium from one of the fluid reservoirs 208. The continuous flow reduces the potential for cells to become entrapped within the membrane of the cross-flow module 564.

Cell seeding on to the implantable differentiation scaffold 312 is achieved by transferring the washed cells from the reservoir 562 to the top surface of the scaffold via the valves 214m, 214j, 214p, and pump 122a. The loss of cells away from the scaffold is minimized by the optional use of a scaffold membrane or mesh 326. Following cell seeding, fresh differentiation media may be introduced into the differentiation/tissue formation chamber 306 through the operation of pump 122b. The differentiation medium is periodically or continuously replaced with fresh differentiation medium from the reservoir system. During a medium replacement step, the supply of fresh medium from one of the fluid reservoirs 208 is balanced by the removal of fluid to the waste reservoir 208f via valve 214u. In between the medium replacement steps, the fluid within the differentiation/tissue formation chamber is continuously or periodically recirculated under the control of pump 122b, valve 214t, and either valve 214r for perfusion through the tissue construct or valve 214s for delivery outside the scaffold membrane 326. This secondary fluid delivery path outside the scaffold membrane is located away from that region of the implantable scaffold that is seeded with cells so as to minimize the potential for damaging sheer stresses that could compromise the formation of cell aggregates. As with the previous embodiments of the fluid flow schematic, environmental conditions within the differentiation/tissue formation chamber are monitored and controlled for the period necessary for the successful formation of the tissue construct, at which time the differentiation/tissue formation chamber of the bioreactor is opened and the construct retrieved for subsequent clinical or research use.

FIG. 23 illustrates an embodiment of the invention where the tissue engineering module as described herein comprises three bioreactors. FIG. 23 illustrates the combined use of the tissue digestion bioreactor of FIG. 19 having an internal tissue digestion chamber 322, with the proliferation bioreactor of FIG. 20 having a proliferation chamber 300, and the differentiation bioreactor of FIG. 21 having a differentiation chamber 306. These bioreactors are operably connected on a tissue engineering module to provide for the automated steps involved in the sequence of tissue digestion, cell proliferation, cell differentiation, and tissue formation.

It is understood by one of skill in the art that the automated tissue engineering system may comprise one or more bioreactors as supported to a housing either by a structural support or by equivalent means. When comprising two or more bioreactors, the bioreactors may be operatively connected or alternatively, independently operable and/or co-operatively operable. Furthermore, each bioreactor may comprise a different internal chambers or the same type of chambers. In a further embodiment, the chambers and/or bioreactors are operably connected to provide for the exchange of fluids, cells and/or tissues between the chambers and/or the bioreactors.

The automated tissue engineering system of the invention is easy to prepare for use. The following sequence is a representative example for the preparation of a cartilage implant based on the use of the tissue engineering system of the present invention for the repair of focal defects in articular cartilage. For this application, the stages of tissue digestion, cell proliferation and cell differentiation/tissue formation are required. The three stages of the tissue engineering process may be accomplished by way of a single bioreactor with multiple chambers or three separate and discrete bioreactors, as shown in FIGS. 17, 18 and 22.

Prior to initiating the tissue engineering sequence, the following reagent compositions are loaded into the reservoirs 208a through 208e in the tissue engineering module via the reservoir injection ports 212. Reagent A is utilized for the digestion of chondrocytes derived from small human articular cartilage biopsies. Reagents B, D and E are utilized for cell proliferation. Reagent C is utilized for differentiation and tissue construct formation.

Reagent A—Digestion Medium: DMEM/F-12, 5% FCS or autologous serum, 1 µg/ml Insulin, 50 µg/ml Ascorbic Acid, 100 IU/100 µg/ml Pen/Strep, 2.5% Hepes Buffer, 0.1% (1 mg/ml) Pronase and 0.025% (0.25 mg/ml) Collagenase, pH 7.4

Reagent B—Proliferation Medium: DMEM/F-12, 10% FCS or autologous serum, 10 µg/ml Ascorbic Acid, 100 IU/100 µg/ml Pen/Strep, 2.5% Hepes Buffer, pH 7.4

Reagent C—Differentiation Medium: DMEM/F-12, 10% FCS or autologous serum, 1 µg/ml Insulin, 50 µg/ml ascorbic acid, 100 IU/100 µg/ml Pen/Strep, 2.5% Hepes Buffer, pH 7.4

Reagent D—PBS Wash Solution: 137 mM NaCl, 3.7 mM KCl, 8 mM $Na_2HPO_4*2H_2O$, 1.5 mM $KH_2PO_4$, in $H_2O$, pH 7.4

Reagent E—Cell Release Solution: 1× Trypsin solution

The above reagents are nominally stable for periods up to several weeks when stored at 4° C. on the tissue engineering module within the system enclosure. Enzymes may be stored lyophilized within the tissue engineering module and hydrated at the time of use. This allows custom enzyme tailoring to the specific tissue engineering application.

A human cartilage biopsy (100-500 mg) is obtained through an arthroscopic surgery from a non-load bearing area on the upper medial femoral condyle. Prior to loading the biopsy into the digestion chamber, the biopsy is weighed and the mass recorded for subsequent data entry into the programming sequence for the base unit. Following mass determination, the biopsy is placed within the digestion chamber and the bioreactor is closed ready for the tissue engineering module to be inserted into the base unit of the tissue engineering system. Once the tissue engineering module is installed, the CPU of the base unit is then programmed via the user interface according to the size of the biopsy and the tissue engineering sequence desired.

On initiation of the programmed automated sequence, pronase/collagenase digestion of the biopsy is commenced by an infusion of Reagent A into the digestion chamber of the bioreactor through the activation of the required flow valves and the operation of the fluid delivery pump. Digestion is performed at 37° C. over a 16 hour period under continuous or intermittent recirculation of Reagent A to keep cells in suspension and to to maximize reagent exposure to the biopsy. This may be followed by two consecutive washing steps in Reagent D. At the end of this digestion sequence, approximately 200,000 to 500,000 cells per 100 mg of biopsy tissue are obtained.

At this point a sample of the digested cells may be retrieved via the sampling port in order to assess cell number and vitality. This biological assessment is typically assessed outside the system by way of a hemocytometer after staining with trypan blue.

Under the automated control of the base unit, the disassociated cells are delivered on to the proliferation substrate or scaffold present in the proliferation chamber of the bioreactor in order to establish a cell seeding density between 2000 cells/$cm^2$ and 15000 cells/$cm^2$. To effect continued proliferation toward confluence, Reagent B is supplied from a reservoir on the tissue engineering module according to a preprogrammed flow profile. The temperature and pH of the medium are monitored to detect deviations from 37° C. and pH 7.4, respectively. In addition, the status of cell proliferation is indirectly assessed by detection of metabolic turnover as a function of time (e.g. pH, $O_2$, $CO_2$, lactic acid and glucose consumption). The level of confluence is further supported by optical monitoring via CCD camera linked to the proliferation probe embedded within the proliferation chamber. Once impending confluence is determined either empirically or by way of sensor-based monitoring, the cells are washed extensively by two consecutive washing steps with Reagent D to remove all culture medium.

Detachment of propagated cells from the proliferation substrate or scaffold is initiated by the transfer of Reagent E from a reservoir within the tissue engineering module into the proliferation chamber. This trypsin solution is present for 5 minutes within the bioreactor whereupon the reaction is stopped by the automatic addition of Reagent B which contains FCS or autologous serum that inhibits enzyme activity. Cell release from the proliferation substrate or scaffold is further enhanced by the application of low frequency impact to the bioreactor via the impact drive or recirculation of the trypsin solution. Once released, a cell washing and filtration step is performed in order to remove the trypsin and to concentrate the cell suspension for subsequent transfer on to the scaffold present in the differentiation/tissue formation bioreactor.

For this application, a bipolar configuration is ideal as this provides for cartilage layer at the articular surface that is connected to a porous scaffold layer, formed of a bone biomaterial such as Skelite™, for integration with the subchondral bone. The preparation of the bipolar construct may be achieved through one of several alternate procedures. The differentiation scaffold may be formed with a pore density gradient that preferentially traps cells at one end creating a region of high cell concentration which promotes the formation of the cartilage layer. Alternately, the scaffold may be previously coated on one end with fibrin gel to preclude cell attachment and cartilage matrix formation in this region. With either approach, the loss of cells away from the scaffold is minimized by the optional use of an encircling membrane or mesh. The flow rate for cell delivery is low to ensure fluid shear does not damage the proliferated cell population. Following the completion of the cell seeding step, fluid flow through the differentiation/tissue formation chamber is stopped to enable the formation of cell aggregates, as this is known to be crucial in terms of successful differentiation. Following this important step, perfusion of Reagent C is performed over the period necessary for tissue formation and maturation in order to optimally supply cells with nutrients and to remove waste products. After this culture period, the cells will have produced extracellular matrix that is substantially identical to that of native human articular cartilage. The properties of the tissue formed can be confirmed by independent external biochemical methods such as collagen typing via SDS-PAGE and gene expression. As a final step in the process, the tissue engineering system provides notification by way of the user interface that the sequence is complete and the tissue engineering module may be removed to harvest the implant. The tissue engineering module or a detachable form of the bioreactor may be transported to the operating room whereupon the bioreactor lid is removed in a sterile field and the implant retrieved for surgical use.

It should be noted that the system of the invention is not limited to a particular type of cell or tissue. For example, a skeletal implant may be prepared for use in the reconstruction of bone defects. In this application, bone marrow could be used as the source of the primary and/or precursor cells required for the tissue engineering process. Accordingly, there is no requirement to perform tissue digestion; hence, the bioreactor may be of the type that only supports proliferation and differentiation. Depending on the available cell population and the required size of the implant, even proliferation may not be required. In this case, the configuration of the bioreactor may be directed to the single stage of cell differentiation and ongoing tissue formation. The final tissue construct would be comprised of an implantable scaffold, which may be composed of a bone biomaterial such as Skelite™, with active bone cells lining the open pores of the scaffold and actively laying down new mineralized matrix (osteoid). Such an implant would be quickly integrated at the implant site thereby accelerating the recovery process.

As a further example of the flexibility of the system, tissue engineered blood vessels may be prepared using culture expanded endothelial cells seeded onto flexible scaffolds of a tubular geometry in the final differentiation stage.

The integrated tissue engineering system of the present invention has several advantages compared to methods and systems of the prior art. In particular, the turnkey operation of the device enables complex tissue engineering procedures to be performed under automated control in the clinic, thereby precluding the need to transport cells to centralized facilities for biological processing. The system is simple to use and obviates the existing time consuming and expensive human tissue culture procedures which often lead to implant contamination and failure. The tissue engineering modules and associated subsystem assemblies may be customized for the type of cell or tissue to be cultured and may be fabricated from any suitable biocompatible and sterilization tolerant material. The entire tissue engineering module or specific components thereof are replaceable and may be considered disposable. The tissue engineering module may be provided in a single-use sterile package that simplifies system set-up and operation in clinical settings.

It is understood by those skilled in the art that the tissue engineering module and device of the present invention can be fabricated in various sizes, shapes and orientation. The device can be fabricated to incorporate a single tissue engineering module or multiple modules in vertical or horizontal formats. Accordingly, the subassemblies can be made to correspond to the spatial format selected for the tissue engineering device. As such different types of tissue engineering can be simultaneously conducted in a single device with each tissue engineering sequence being automatically monitored and controlled on an individual basis. It is also within the scope of the invention to have a plurality of automated tissue engineering systems operating and networked under the control of a remote computer.

Although preferred embodiments of the invention have been described herein in detail, it will be understood by those skilled in the art that variations may be made thereto without departing from the spirit of the invention or the scope of the appended claims.

We claim:

1. A portable tissue and/or cell culture engineering module, the module comprising;
    at least one bioreactor, said bioreactor facilitating cell culture and/or tissue engineering functions;
    a fluid containment system in fluid communication with said at least one bioreactor;

a heating and/or mixing chamber to heat and/or mix fluids flowing to said at least one bioreactor; and one or more sensors configured to actively detect environmental conditions and cell metabolic turnover as a function of time with respect to the progression of the cell culture and/or tissue growth in said at least one bioreactor, said one or more sensors operatively generate signals to a central and/or onboard microprocessor to actively monitor and actively adjust the changing environmental conditions responsive to requirements of different stages of the cell culture and/or tissue development until completion of cell culture and/or tissue growth.

2. The module of claim 1, wherein said at least one bioreactor comprises:

a bioreactor housing having one or more ports for media flow; and at least one chamber defined within said bioreactor housing for receiving at least one of said cells and/or tissues and facilitating said cell culture and/or tissue engineering functions.

3. The module of claim 2, wherein said at least one chamber houses one or more substrates and/or scaffolds.

4. The module of claim 2, wherein said at least one chamber comprises two or more chambers that are operably connected within said at least one bioreactor.

5. The module of claim 1, wherein said at least one bioreactor comprises two or more bioreactors that are operably connected.

6. The module of claim 4, wherein at least one of said two or more chambers, and said at least one bioreactor are independently operable and/or co-operatively operable.

7. The module of claim 6, wherein said at least one bioreactor comprises a first bioreactor, a second bioreactor and a third bioreactor, said first bioreactor containing a tissue digestion chamber, said second bioreactor containing a culture/proliferation chamber, said third bioreactor containing a differentiation/tissue formation chamber, and wherein said first, second and third bioreactors are operatively connected.

8. The module of claim 4, wherein said at least one chamber and/or said at least one bioreactor are operably connected to provide for the exchange of fluids, cells and/or tissues between said two are more chambers and/or bioreactors.

9. The module of claim 2, wherein said at least one chamber contains a plurality of zones to contain a plurality of substrates and scaffolds.

10. The module of claim 1, wherein a plurality of fluid flow control valves are provided in operable connection with said fluid containment system to control the flow of fluid with said fluid containment system and said at least one bioreactor.

11. The module of claim 10, wherein said module additionally comprises one or more pump units in connection with said fluid containment system for the pumping of fluid throughout said fluid containment system.

12. The module of claim 1, wherein one or more gas exchange membranes are provided within one of or between said fluid containment system and said at least one bioreactor, said gas exchange membranes permitting the transfer of gaseous products into or out of fluid flowing to or resident in said bioreactor.

13. The module of claim 1, wherein said module additionally comprises a thermoelectric element in operable connection with said at least one bioreactor.

14. The module of claim 1, wherein said module additionally comprises one or more microprocessors in operable connection with said one or more sensors.

15. The module of claim 1, wherein said module additionally comprises one or more access ports, said one or more access ports being operatively linked with said at least one bioreactor and said fluid containment system, said one or more access ports providing for sterile loading or removal of cells, fluids, cell and tissue culture media, growth factors, pharmaceutical agents, quality control reagents, quality control samples and/or other materials.

16. The module of claim 1, wherein said at least one bioreactor is integrally mounted or detachable.

17. The module of claim 1, wherein a camera is provided for visual inspection within said at least one bioreactor.

18. The module of claim 1, wherein said module additionally comprises an identifying element for identification and tracking in a clinical or experimental environment for correct patient identification and/or clinical billing.

19. The module of claim 18, configured for providing a patient personalized tissue and/or cell culture.

20. The module of claim 1, wherein said module is sterilizable before use and disposable after use.

21. The module of claim 1, wherein said environmental conditions are selected from the group consisting of pH, temperature, dissolved gases and combinations thereof.

22. The module of claim 1, wherein metabolic turnover is detected by assessing one or more of pH, $O_2$, $CO_2$, lactic acid and glucose consumption.

\* \* \* \* \*